US010597416B2

(12) United States Patent
Colacot et al.

(10) Patent No.: US 10,597,416 B2
(45) Date of Patent: *Mar. 24, 2020

(54) COMPLEXES

(71) Applicant: Johnson Matthey Public Limited Company, London (GB)

(72) Inventors: Thomas John Colacot, Cherry Hill, NJ (US); Carin C. C. Johansson Seechurn, Cambridge (GB); Sebastien Laurent Parisel, La Garenne Colombes (FR)

(73) Assignee: Johnson Matthey PLC, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/136,685

(22) Filed: Sep. 20, 2018

(65) Prior Publication Data

US 2019/0016742 A1 Jan. 17, 2019

Related U.S. Application Data

(62) Division of application No. 13/806,575, filed as application No. PCT/GB2011/051171 on Jun. 22, 2011, now Pat. No. 10,167,305.

(60) Provisional application No. 61/357,744, filed on Jun. 23, 2010.

(51) Int. Cl.
| | | |
|---|---|---|
| C07F 15/00 | (2006.01) | |
| B01J 31/12 | (2006.01) | |
| C07F 17/02 | (2006.01) | |
| B01J 31/22 | (2006.01) | |
| B01J 31/24 | (2006.01) | |
| C07F 15/04 | (2006.01) | |

(52) U.S. Cl.
CPC ........... C07F 17/02 (2013.01); B01J 31/2286 (2013.01); B01J 31/2291 (2013.01); B01J 31/2295 (2013.01); B01J 31/24 (2013.01); B01J 31/2404 (2013.01); C07F 15/006 (2013.01); C07F 15/04 (2013.01); B01J 2231/4205 (2013.01); B01J 2231/4211 (2013.01); B01J 2231/4227 (2013.01); B01J 2231/4283 (2013.01); B01J 2531/0205 (2013.01); B01J 2531/824 (2013.01); B01J 2531/842 (2013.01); B01J 2531/847 (2013.01)

(58) Field of Classification Search
CPC ....... C07F 15/006; B01J 31/12; B01J 31/0255
USPC ..................... 556/22, 13; 502/155
See application file for complete search history.

(56) References Cited

U.S. PATENT DOCUMENTS 10,167,305 B2 * 1/2019 Colacot .................. C07F 17/02

FOREIGN PATENT DOCUMENTS

| WO | WO 98/22424 A1 | 5/1998 |
|---|---|---|
| WO | WO 99/47474 A1 | 9/1999 |
| WO | WO 01/16057 A1 | 3/2001 |
| WO | WO 2003/000666 A1 | 1/2003 |
| WO | WO 2007/109355 A2 | 9/2007 |
| WO | WO 2008/016956 A2 | 2/2008 |

OTHER PUBLICATIONS 1.3.1.7.2 Verbindungen des Typs 3LNi(D)R—Compounds of the 3LNi(D)R Type in: Gmelin Handbuch der Anorganischen Chemie Ergäzungswerk zur 8. Auflage Band 17 Nickel-Organische Verbindungen Teil 2, 1974, Springer Verlag, pp. 29-40.
Åkermark et al., Ligand Effetcs and Nucleophillic Addition of (N3-Allyl)palladium Complexes, a Carbon-13 Nuclear Magnetic Resonance Study, Organometallics, 1987, vol. 6, pp. 620-628.
Auburn et al., Asymmetric Synthesis, Assymmetric Catalytic Allylation Using Palladium Chiral Phosphine Complexes, J. Am. Chem. Soc., 1985, vol. 107, pp. 2033-2046.
Carturan, Activation of H2 With Allylpalladium(II) Derivatives, Selective Catalytic Hydrogenation of Allene to Propene, Journal of Organometallic Chemistry, 1978, vol. 157, pp. 475-481.
Chartoire et al., Highly Active Well-Defined Palladium Precatalysts for the Efficient Amination of Aryl Chlorides, Organometallics, 2011, vol. 30, pp. 4432-4436.
Clark, H.C., et al, Preliminary Communication Insertion of Hexafluoro-2-Butyne Into a Palladium-Allyl Bond, Journal of Organometallic Chemistry. 1972, vol. 39, p. C13.
Dent. et al., Some Observations on the Preparation of Tr-Allylic Palladium Chloride Complexes, J. Am. Chem. Soc., 1964, pp. 1585-1588.
Dietrich et al., Amidoamine-based Dendrimers With End-Grafted Pd-Fe Units: Synthesis, Characterization and Their Use in the Heck Reaction, Journal of Organometallic Chemistry, 2011, vol. 696, pp. 739-747.

(Continued)

*Primary Examiner* — Charanjit Aulakh
(74) *Attorney, Agent, or Firm* — BakerHostetler

(57) ABSTRACT

The present invention provides a complex of formula (1), $$\underset{R_3}{\overset{R_2}{\diagdown}}\!\!\!\overset{R_1}{\diagup}\!\!\!\underset{X}{\overset{|}{M}}\!\!\!\!-\!\!\!(R_4)_n \qquad (1)$$

wherein, M is palladium or nickel, $R_1$ and $R_2$ are independently organic groups having 1-20 carbon atoms, or $R_1$ and $R_2$ are linked to form a ring structure with the phosphorus atom, $R_3$ is selected from the group consisting of substituted and unsubstituted aryl, substituted and unsubstituted heteroaryl, and substituted and unsubstituted metallocenyl, $R_4$ is an organic group having 1-20 carbon atoms, n is 0, 1, 2, 3, 4 or 5, and X is an anionic ligand. The invention also provides a process for the preparation of the complex, and its use in carbon-carbon or carbon-nitrogen coupling reactions.

10 Claims, 2 Drawing Sheets

(56) References Cited

OTHER PUBLICATIONS

Dreher et al., Efficient Cross-Coupling of Secondary Alkyltrifluoroborates With Aryl Chlorides-Reaction Discovery Using Parallel Microscale Experimentation, J. Am. Chem. Soc., 2008 vol. 130, pp. 9257-9259.
Fitton, P. et al., Oxidative Additions to Palladium(0), Chemical Communications, 1968, vol. 1, p. 7.
Grabulosa et al., Allylpalladium Complexes With P-Stereogenic Monodentate Phosphines, Application in the Asymmetric Hydrovinylation of Styrene, Organometallics, 2005, vol. 24, pp. 4961-4973.
Grabulosa et al., Better Performance of Monodentate P-Stereogenic Phosphanes Compared to Bidentate Analogues in Pd-Catalyzed Asymmetric Allylic Alkylations, Eur. J. Inorg. Chem, 2010, pp. 3372-3383.
Guram et al., New Air-Stable Catalysts for General and Efficient Suzuki-Miyaura Cross-Coupling Reactions of Heteroaryl Chlorides, Organic Letters, 2006, vol. 8, No. 9, pp. 1787-1789.
Hartwig, JF et al., Distinct Mechanisms for the Oxidative Addition of Chloro-, Bromo-, and Iodoarenes to a Bisphosphine Palladium(0) Complex With Hindered Ligands., J. Am. Chem. Soc, 2005, vol. 127, p. 6944.
Hartwig, JF et al., Palladium-Catalyzed C—O Coupling Involving Unactivated Aryl Halides, Sterically Induced Reductive Elimination to Form the C—O Bond in Diaryl Ethers, J. Am. Chem. Soc., 1999, vol. 121, p. 3225.
He et al., Stereospecific Suzuki Cross-Coupling of Alkyl α-Cyanohydrin Triflates, J. Am. Chem. Soc., 2010, vol. 132, pp. 2524-2525.
International Search Report from PCT/GB2011/051171 dated Oct. 19, 2011.
Kisanga et al., Develoment, Synthetic Scope, and Mechanistic Studies of the Palladium-Catalyzed Cycloisomerization of Functionalized 1,6-Dienes in the Presence of Silane, J. Am. Chem. Soc., 2000, vol. 122, pp. 10017-10026.
Krasovskiy et al., Zn-Mediated, Pd-Catalyzed Cross-Couplings in Water at Room Temperature Without Prior Formation of Organozinc Reagents, J. Am. Chem. Soc., 2009, vol. 131, pp. 15592-15593.
Kurosawa, H., et al., 1-3-η-Allylpalladium (II) and Platinum (II) Complexes Containing Tris (2,6-dimethoxyphenyl) Phosphine Ligand, The Journal of the Chemical Society of Japan, 1987, vol. 60, p. 3564.
Lamac et al., Synthesis, Coordination and Catalytic Utility of Novel Phosphanyl-Ferrocenecarboxylic Ligands Combining Planar and Central Chirality, Eur. J. Inorg. Chem, 2007, pp. 2274-2287.
Marion et al., Modified (NHC)Pd(allyl)Cl(NHC=N-Heterocyclic Carbene) Complexes for Room-Temperature Suzuki-Miyaura and Buchwald-Hartwig Reactions, J. Am. Chem. Soc., 2006, vol. 128, pp. 4101-4111.
Nicholson et al., The Mechanism of Formation of π-Allylic Plaladium(II) Chlorides from Sodium Chloropalladite, Allylic Chlorides, and Carbon Monoxide Reacting in Aqueous Methanol, J. Chem. Soc.: Chem. Commun., 1966, pp. 174-175.
Nolan, SP et al., Well-Defined, Air Stable (NHC)pd(Allyl)Cl(NHC= N-Heterocyclic Carbene) Catalysts for the Arylation of Ketones, Organic Letters, 2002, vol. 4, p. 4054.
Ohmura et al., Switch of Regioselectivity in Palladium-Catalyzed Silaboration of Terminal Alkynes by Ligand-Dependent Control of reductive Elimination, J. Am. Chem. Soc., 2010, vol. 132, pp. 12194-12196.
Oslinger et al., Further N.M.R. Studies of the Dynamic Stereochemistry of π-Allylic Palladium(II)—Tertiary Phosphine Systems, Can. J. Chem., 1973, vol. 51, pp. 274-287.
Powell, J. et al., Further N.M.R. Studies of the Dynamic Stereochemistry of π-Allylic Palladium(II)—Tertiary Phosphine Systems, Can. J. Chem. 1973, vol. 51, p. 284.
Reid, et al., Reactions of Free Radicals with η3-Allylpalladium(II) Complexes: Cyclohexyl Radicals, Journal of Organometallic Chemistry, 2004, vol. 689, pp. 1257-1264.
TeleshTeleshev, At. et al., Thin-Layer Chromatography As a Method for Monitoring in the Synthesis of Catalytic Systems, Moscow Pedagog. Inst. 1979, vol. 34, p. 348.
Tolkunova et al., Preparation of Complexes of π-Allylpalladium Chloride With Ferrocenylphospine Ligands and Investigation of Retarded Rotation Around Pd-P Bond, Bulletin of the Academy of Sciences of the USSR, Division Chemical Sciences, vol. 30, No. 10, 1981, pp. 1826-1830.
Van Leeuwen et al., Magnetic Non-Equivalence in Substituted Allylpalladium Compounds in Relation to Molecular Rearrangements, J. Organometal. Chem., 1971, vol. 29, pp. 433-442.
Widenhoefer, RA et al., Development, Synthetic Scope, and Mechanistic Studies of the Palladium-Catalyzed Cycloisomerization of Functionalized 1,6-Dienes in the Presence of Silane, J. Am. Chem. Soc. 2000, vol. 122, p. 10019.
Xu, N. et al., Preparation of Merrifield Resin-Supported Diphenylphosphinobiphenyl palladium catalyst and it application to Suzuki reactions, Youji Huaxue, 2005, vol. 25, p. 458.

* cited by examiner

COMPLEXES

CROSS REFERENCE TO RELATED APPLICATIONS

This application is a divisional of U.S. patent application Ser. No. 13/806,575, filed Mar. 11, 2013, which is the National Stage of International Patent Application No. PCT/GB2011/051171, filed Jun. 22, 2011, which claims priority from U.S. Provisional Patent Application No. 61/357,744, filed Jun. 23, 2010, the disclosures of each of which are incorporated herein by reference in their entireties for any and all purposes.

The present invention relates to transition metal complexes and, in particular, to π-allyl complexes, such as π-allylpalladium and π-allylnickel complexes. The invention also relates to the use of the transition metal complexes in coupling reactions.

In many transitions metal mediated reactions, the active catalyst is formed in situ by the additional of a transition metal precursor, such as $Pd(OAc)_2$ or $Pd_2(dba)_3$, and the ligand in question. In these processes, an excess amount of ligand is usually required, which can be disadvantageous if the cost of the ligand is high, in addition to storage and handling difficulties if the ligand is air sensitive.

As an alternative to preparing the active catalyst in situ, it is possible to prepare pre-formed transition metal complexes which comprise a well-defined transition metal atom to ligand ratio.

WO99/47474 and WO01/16057 (both to Ciba Speciality Chemicals Holdings Inc.) describe various allylpalladium complexes containing tertiary phosphine ligands. The ligands exemplified are trialkylphosphine ligands.

The present inventors have developed complexes which overcome problems associated with the prior art.

SUMMARY OF THE INVENTION

The inventors have discovered a class of π-allylpalladium and π-allylnickel complexes, which may be employed to effect a variety of reactions, such as C—N and C—C bond formation reactions. In certain embodiments, the π-allyl complexes are highly active catalysts. In certain embodiments, the π-allyl complexes are stable to air and moisture at ambient temperatures.

In one aspect, the present invention provides a complex of formula (1)

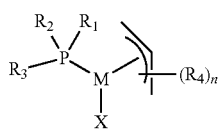

(1)

wherein,
M is palladium or nickel,
$R_1$ and $R_2$ are independently organic groups having 1-20 carbon atoms, or $R_1$ and $R_2$ are linked to form a ring structure with the phosphorus atom,
$R_3$ is selected from the group consisting of substituted or unsubstituted aryl, substituted or unsubstituted heteroaryl, and substituted and unsubstituted metallocenyl,
$R_4$ is an organic group having 1-20 carbon atoms,
n is 0, 1, 2, 3, 4 or 5,
X is an anionic ligand.

In addition, described more fully below is a process to prepare the π-allyl complexes, as well as processes that employ such complexes.

Definitions

The point of attachment of a moiety or substituent is represented by "—". For example, —OH is attached through the oxygen atom.

"Alkyl" refers to a straight-chain or branched saturated hydrocarbon group. In certain embodiments, the alkyl group may have from 1-20 carbon atoms, in certain embodiments from 1-15 carbon atoms, in certain embodiments, 1-8 carbon atoms. Unless otherwise specified, the alkyl group may be attached at any suitable carbon atom and, if substituted, may be substituted at any suitable atom. The alkyl group may be unsubstituted or substituted. Typical alkyl groups include but are not limited to methyl, ethyl, n-propyl, iso-propyl, n-butyl, iso-butyl, sec-butyl, tert-butyl, n-pentyl, n-hexyl and the like.

The term "cycloalkyl" is used to denote a saturated carbocyclic hydrocarbon radical. In certain embodiments, the cycloalkyl group may have from 3-15 carbon atoms, in certain embodiments, from 3-10 carbon atoms, in certain embodiments, from 3-8 carbon atoms. Unless other specified, the cycloalkyl group may be attached at any suitable carbon atom and, if substituted, may be substituted at any suitable atom. The cycloalkyl group may unsubstituted or substituted. Typical cycloalkyl groups include but are not limited to cyclopropyl, cyclobutyl, cyclopentyl, cyclohexyl and the like.

"Alkoxy" refers to an optionally substituted group of the formula alkyl-O— or cycloalkyl-O—, wherein alkyl and cycloalkyl are as defined above.

"Alkoxyalkyl" refers to an optionally substituted group of the formula alkoxy-alkyl-, wherein alkoxy and alkyl are as defined above.

"Aryl" refers to an aromatic carbocyclic group. The aryl group may have a single ring or multiple condensed rings. In certain embodiments, the aryl group can have from 6-20 carbon atoms, in certain embodiments from 6-15 carbon atoms, in certain embodiments, 6-12 carbon atoms. The aryl group may be unsubstituted or substituted. Unless otherwise specified, the aryl group may be attached at any suitable carbon atom and, if substituted, may be substituted at any suitable atom. Examples of aryl groups include, but are not limited to, phenyl, naphthyl, anthracenyl and the like.

"Arylalkyl" refers to an optionally substituted group of the formula aryl-alkyl-, where aryl and alkyl are as defined above.

"Halo" or "hal" refers to —F, —Cl, —Br and —I.

"Heteroalkyl" refers to a straight-chain or branched saturated hydrocarbon group wherein one or more carbon atoms are independently replaced with one or more heteroatoms (e.g. nitrogen, oxygen, phosphorus and/or sulfur atoms). The heteroalkyl group may be unsubstituted or substituted. Unless otherwise specified, the heteroalkyl group may be attached at any suitable atom and, if substituted, may be substituted at any suitable atom. Examples of heteroalkyl groups include but are not limited to ethers, thioethers, primary amines, secondary amines, tertiary amines and the like.

"Heterocycloalkyl" refers to a saturated cyclic hydrocarbon group wherein one or more carbon atoms are independently replaced with one or more heteroatoms (e.g. nitrogen, oxygen, phosphorus and/or sulfur atoms). The heterocycloalkyl group may be unsubstituted or substituted. Unless otherwise specified, the heterocycloalkyl group may be attached at any suitable atom and, if substituted, may be substituted at any suitable atom. Examples of heterocycloalkyl groups include but are not limited to epoxide, morpholinyl, piperadinyl, piperazinyl, thirranyl, pyrrolidinyl, pyrazolidinyl, imidazolidinyl, thiazolidinyl, thiomorpholinyl and the like.

"Heteroaryl" refers to an aromatic carbocyclic group wherein one or more carbon atoms are independently replaced with one or more heteroatoms (e.g. nitrogen, oxygen, phosphorus and/or sulfur atoms). The heteroaryl group may be substituted or unsubstituted. Unless otherwise specified, the heteroaryl group may be attached at any suitable atom and, if substituted, may be substituted at any suitable atom. Examples of heteroaryl groups include but are not limited to thienyl, furanyl, pyrrolyl, imidazolyl, pyrazolyl, thiazolyl, isothiazolyl, oxazolyl, isoxazolyl, triazolyl, thiadiazolyl, thiophenyl, oxadiazolyl, pyridinyl, pyrimidyl, benzoxazolyl, benzthiazolyl, benzimidazolyl, indolyl, quinolinyl and the like.

"Substituted" refers to a group in which one or more hydrogen atoms are each independently replaced with substituents (e.g. 1, 2, 3, 4, 5 or more) which may be the same or different. Examples of substituents include but are not limited to -halo, —C(halo)$_3$, —R$^a$, =O, =S, —O—R$^a$, —S—R$^a$, —NR$^a$R$^b$, =NR$^a$, =N—OR$^a$, —CN, —SCN, —NCS, —NO$_2$, —C(O)—R$^a$, —COOR$^a$, —C(S)—R$^a$, —C(S)OR$^a$, —S(O)$_2$OH, —S(O)$_2$—R$^a$, —S(O)$_2$NR$^a$R$^b$, —O—S(O)—R$^a$ and —CONR$^a$R$^b$; wherein R$^a$ and R$^b$ are independently selected from the groups consisting of H, alkyl, aryl, arylalkyl, heteroalkyl, heteroaryl, or R$^a$ and R$^b$ together with the atom to which they are attached form a heterocycloalkyl group, and wherein R$^a$ and R$^b$ may be unsubstituted or further substituted as defined herein.

"Metallocenyl" refers to a transition metal complex group wherein a transition metal atom or ion is "sandwiched" between two rings of atoms. The metallocenyl group may be substituted or unsubstituted. Unless otherwise specified, the metallocenyl group may be attached at any suitable atom and, if substituted, may be substituted at any suitable atom. Examples of transition metal atoms or ions include but are not limited to chromium, manganese, cobalt nickel and iron. An example of a suitable ring of atoms is a cyclopentadienyl ring. An example of a metallocenyl group includes but is not limited to ferrocenyl, which comprises a Fe(II) ion sandwiched between two cyclopentadienyl rings, wherein each cyclopentadienyl ring may be independently unsubstituted or substituted.

BRIEF DESCRIPTION OF THE DRAWINGS

The invention will now be described by way of example only and with reference to the following drawings in which.

DETAILED DESCRIPTION

Figure 1:
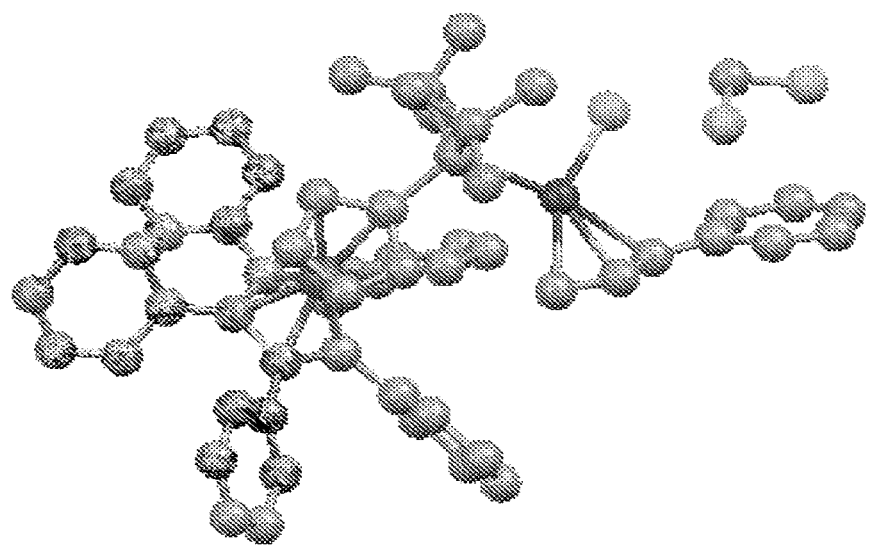
FIG. 1 is an X-ray crystal structure of Pd(π-cinnamyl) QPhosCl.

In one aspect, the present invention provides a complex of formula (1)

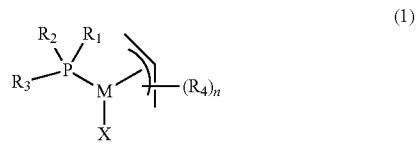

wherein,

M is palladium or nickel,

R$_1$ and R$_2$ are independently organic groups having 1-20 carbon atoms, or R$_1$ and R$_2$ are linked to form a ring structure with the phosphorus atom, R$_3$ is selected from the group consisting of substituted and unsubstituted aryl, substituted and unsubstituted heteroaryl and substituted and unsubstituted metallocenyl, R$_4$ is an organic group having 1-20 carbon atoms, n is 0, 1, 2, 3, 4 or 5, X is an anionic ligand.

The metal M is a precious metal selected from palladium or nickel. In one particularly preferred embodiment, M is palladium.

When M is palladium, M may be Pd(II). When M is nickel, M may be Ni(II).

PR$_1$R$_2$R$_3$ is a monodentate tertiary phosphine ligand. In one embodiment, R$_1$ and R$_2$ are independently selected from the group consisting of substituted and unsubstituted straight-chain alkyl, substituted and unsubstituted branched-chain alkyl, substituted and unsubstituted cycloalkyl, substituted and unsubstituted aryl, and substituted and unsubstituted heteroaryl wherein the heteroatoms are selected from sulfur, nitrogen and oxygen. R$_1$ and R$_2$ may independently be substituted or unsubstituted branched- or straight-chain alkyl groups such as methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantly, or aryl groups such as phenyl, naphthyl or anthracyl. In one embodiment, the alkyl groups may be optionally substituted with one or more substituents such as halide (F, Cl, Br or I) or alkoxy groups, e.g. methoxy, ethoxy or propoxy. The aryl group may be optionally substituted with one or more (e.g. 1, 2, 3, 4, or 5) substituents such as halide (F, Cl, Br or I), straight- or branched-chain alkyl (e.g. C$_1$-C$_{10}$), alkoxy (e.g. C$_1$-C$_{10}$ alkoxy), straight- or branched-chain (dialkyl)amino (e.g. C$_1$-C$_{10}$ dialkyl)amino), heterocycloalkyl (e.g. C$_{3-10}$ heterocycloalkyl groups, such as morpholinyl and piperadinyl) or tri(halo)methyl (e.g. F$_3$C—). Suitable substituted aryl groups include but are not limited to 4-dimethylaminophenyl, 4-methylphenyl, 3,5-dimethylphenyl, 4-methoxyphenyl and 4-methoxy-3,5-dimethylphenyl. Substituted or unsubstituted heteroaryl groups such as pyridyl may also be used. In an alternative embodiment, R$_1$ and R$_2$ are linked to form a ring structure with the phosphorus atom, preferably 4- to 7-membered rings. Preferably, R$_1$ and R$_2$ are the same and are tert-butyl, cyclohexyl, phenyl or substituted phenyl groups. More preferably, R$_1$ and R$_2$ are both tert-butyl.

R$_3$ is selected from the group consisting of substituted or unsubstituted aryl, substituted or unsubstituted heteroaryl, and substituted and unsubstituted metallocenyl.

In one embodiment, R$_3$ is a substituted or unsubstituted aryl. The aryl group may be optionally substituted with one or more (e.g. 1, 2, 3, 4, or 5) substituents such as halide (F, Cl, Br or I), straight- or branched-chain alkyl (e.g. C$_1$-C$_{10}$), alkoxy (e.g. C$_1$-C$_{10}$ alkoxy), substituted or unsubstituted aryl, straight- or branched-chain (dialkyl)amino (e.g. C$_1$-C$_{10}$ dialkyl)amino), heterocycloalkyl (e.g. $C_{3-10}$ heterocycloalkyl groups, such as morpholinyl and piperadinyl) or tri(halo)methyl (e.g. $F_3C—$). In one embodiment, $R_3$ is preferably phenyl or 2-, 3- or 4-dimethylaminophenyl.

In another embodiment, $R_3$ is a substituted or unsubstituted heteroaryl, for example, substituted or unsubstituted furanyl, thiophenyl, pyrrolyl, pyridinyl or quinolinyl.

In an alternative embodiment, $R_3$ is a substituted or unsubstituted metallocenyl group. The metallocenyl group may have a structure of formula (2):

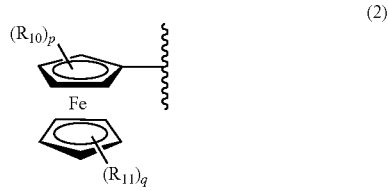

(2)

wherein, $R_{10}$ and $R_{11}$ are independently organic groups having 1-20 carbon atoms, p is 0, 1, 2, 3 or 4, and q is 0, 1, 2, 3, 4 or 5.

Metallocenyl groups of formula (2) are described in WO02/11883 which is incorporated by reference in its entirety for all purposes.

$R_{10}$ is an organic group having 1-20 carbon atoms, preferably 1-15 carbon atoms, more preferably 1-10 carbon atoms and even more preferably 1-8 carbon atoms. The number of $R_{10}$ groups range from 0 to 4 i.e. p is 0, 1, 2, 3 or 4. In certain embodiments, p is 0. When p is 2, 3 or 4, each $R_{10}$ may be the same or different.

$R_{10}$ may be substituted or unsubstituted alkyl, aryl, (alkyl)HN—, (dialkyl)N—, (dialkyl)amino-alkyl- or alkoxyalkyl. The substituted or unsubstituted alkyl group may be a substituted or unsubstituted $C_1$-$C_{20}$ alkyl group, preferably a substituted or unsubstituted $C_1$-$C_{10}$ alkyl and more preferably a substituted or unsubstituted $C_1$-$C_8$ alkyl, which may be branched or straight-chain, such as methyl, ethyl, n-propyl, iso-propyl, n-butyl, iso-butyl, sec-butyl, tert-butyl, pentyl, hexyl, heptyl, octyl, nonyl, decyl or stearyl. The aryl group may be substituted with one or more (e.g. 1, 2, 3, 4, or 5) substituents such as halide (F, Cl, Br or I), straight- or branched-chain alkyl (e.g. $C_1$-$C_{10}$), alkoxy (e.g. $C_1$-$C_{10}$ alkoxy), straight- or branched-chain (dialkyl)amino (e.g. ($C_1$-$C_{10}$ dialkyl)amino), heterocycloalkyl (e.g. $C_{3-10}$ heterocycloalkyl groups, such as morpholinyl and piperadinyl) or tri(halo)methyl (e.g. $F_3C—$). Suitable aryl groups are phenyl, naphthyl, 2-, 3- or 4-methoxyphenyl, or 2-, 3- or 4-halophenyl. The substituted or unsubstituted (alkyl)HN— group may be substituted or unsubstituted methylamino, ethylamino or propylamino. The substituted or unsubstituted (dialkyl)N— group may be dimethylamino, diethylamino or dipropylamino. The substituted or unsubstituted (dialkyl) amino-alkyl- group may be 1-dialkylaminoethyl. The substituted or unsubstituted alkoxyalkyl group may be methoxymethyl, or 1-alkoxyethyl, such as methoxyethyl or ethoxyethyl.

$R_{11}$ is an organic group having 1-20 carbon atoms, preferably 1-10 carbon atoms and more preferably 1-8 carbon atoms. The number of $R_{11}$ groups ranges from 0 to 5 i.e. q is 0, 1, 2, 3, 4 or 5. In certain embodiments, q is 4 or 5. When q is 2, 3, 4, or 5, each $R_{11}$ may be the same or different.

$R_{11}$ may be substituted or unsubstituted alkyl or aryl. The substituted or unsubstituted alkyl group may be a substituted or unsubstituted $C_1$-$C_{20}$ alkyl group, preferably a substituted or unsubstituted $C_1$-$C_{10}$ alkyl and more preferably a substituted or unsubstituted $C_1$-$C_8$ alkyl, which may be branched or straight-chain, such as methyl, ethyl, n-propyl, iso-propyl, n-butyl, iso-butyl, sec-butyl, tert-butyl, pentyl, hexyl, heptyl, octyl, nonyl, decyl, dodecyl or stearyl. The aryl group may be unsubstituted or substituted with one or more (e.g. 1, 2, 3, 4, or 5) substituents such as halide (F, Cl, Br or I), straight- or branched-chain alkyl (e.g. $C_1$-$C_{10}$), alkoxy (e.g. $C_1$-$C_{10}$ alkoxy), straight- or branched-chain (dialkyl)amino (e.g. $C_1$-$C_{10}$ dialkyl)amino), heterocycloalkyl (e.g. $C_{3-10}$ heterocycloalkyl groups, such as morpholinyl and piperadinyl) or tri(halo)methyl (e.g. $F_3C—$). Suitable aryl groups are phenyl, naphthyl, 2-, 3- or 4-methoxyphenyl, 2-, 3- or 4-halophenyl, 2- 3- or 4-methylphenyl or 2-, 3- or 4-$F_3C$-phenyl.

In one preferred embodiment, the metallocenyl group has a structure of formula (3):

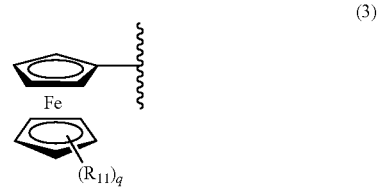

(3)

wherein $R_{11}$ and q are as defined above. In another preferred embodiment, $R_{11}$ is selected from the group consisting of phenyl, naphthyl, 2-, 3- or 4-methoxyphenyl, 2-, 3- or 4-halophenyl, 2- 3- or 4-methylphenyl or 2-, 3- or 4-$F_3C$-phenyl, and q is 4 or 5. In yet another preferred embodiment, $R_{11}$ is selected from the group consisting of phenyl, 2-, 3- or 4-methoxyphenyl, 2- 3- or 4-methylphenyl or 2-, 3- or 4-$F_3C$-phenyl, and q is 4 or 5.

In one particularly preferred embodiment, the metallocenyl group has a structure of formula (4):

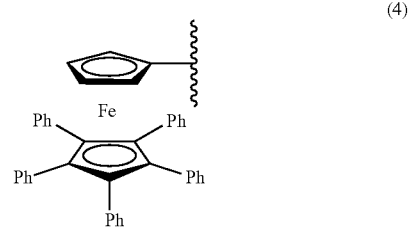

(4)

In one especially preferred embodiment, $PR_1R_2R_3$ is:

(a) the sterically demanding electron rich QPhos ligand i.e. $R_1$ and $R_2$ are tert-butyl and $R_3$ is a metallocenyl group of formula (4);

(b) Amphos i.e. $R_1$ and $R_2$ are tert-butyl and $R_3$ is 4-dimethylaminophenyl; or (c) $P^tBu_2Ph$ i.e. $R_1$ and $R_2$ are tert-butyl and $R_3$ is phenyl.

The M atom in the complex of formula (1) is coordinated to an optionally substituted allyl group. $R^4$ is an organic group having 1-20 carbon atoms, preferably 1-10 carbon atoms and more preferably 1-8 carbon atoms. The number of $R_4$ groups ranges from 0 to 5 i.e. n is 0, 1, 2, 3, 4 or 5. When n is 2, 3, 4 or 5, each of $R_4$ may be the same or different. In certain embodiments, when n is 2, 3, 4, or 5, $R_4$ is the same. In certain embodiments, n is 0 i.e. the allyl group is unsubstituted. In certain embodiments, n is 1. In certain embodiments, n is 2, wherein each $R_4$ is the same or different.

$R_4$ may be selected from the group consisting of substituted and unsubstituted straight-chain alkyl, substituted and unsubstituted branched-chain alkyl, substituted and unsubstituted cycloalkyl, substituted and unsubstituted aryl, and substituted and unsubstituted heteroaryl wherein the heteroatoms are selected from sulfur, nitrogen and oxygen. In one embodiment, $R^4$ is selected from the group consisting of substituted and unsubstituted straight-chain alkyl, substituted and unsubstituted branched-chain alkyl, and substituted and unsubstituted cycloalkyl. In another embodiment, $R_4$ is selected from the group consisting of substituted and unsubstituted aryl, and substituted and unsubstituted heteroaryl wherein the heteroatoms are selected from sulfur, nitrogen and oxygen. $R_4$ may be substituted or unsubstituted branched- or straight-chain alkyl groups such as methyl, ethyl, n-propyl, iso-propyl, n-butyl, iso-butyl, sec-butyl, tert-butyl, pentyl, hexyl, heptyl, octyl, nonyl, decyl, dodecyl or stearyl, cycloalkyl groups such as cyclopropyl, cyclobutyl, cyclopentyl, cyclohexyl or adamantly or aryl groups such as phenyl, naphthyl or anthracyl. In one embodiment, the alkyl groups may be optionally substituted with one or more substituents such as halide (F, Cl, Br or I), alkoxy groups, e.g. methoxy, ethoxy or propoxy. The aryl group may be optionally substituted with one or more (e.g. 1, 2, 3, 4, or 5) substituents such as halide (F, Cl, Br or I), straight- or branched-chain alkyl (e.g. $C_1$-$C_{10}$), alkoxy (e.g. $C_1$-$C_{10}$ alkoxy), straight- or branched-chain (dialkyl)amino (e.g. $C_1$-$C_{10}$ dialkyl)amino) heterocycloalkyl (e.g. $C_{3-10}$ heterocycloalkyl groups, such as morpholinyl and piperadinyl) or tri(halo)methyl (e.g. $F_3C$—). Suitable substituted aryl groups include but are not limited to 2-, 3- or 4-dimethylaminophenyl, 2-, 3- or 4-methylphenyl, 2,3- or 3,5-dimethylphenyl, 2-, 3- or 4-methoxyphenyl and 4-methoxy-3,5-dimethylphenyl. Substituted or unsubstituted heteroaryl groups such as pyridyl may also be used. In one embodiment, each $R_4$ is independently a methyl, phenyl or substituted phenyl group.

Suitable optionally substituted allyl groups as coordinated to the M atom are shown below:

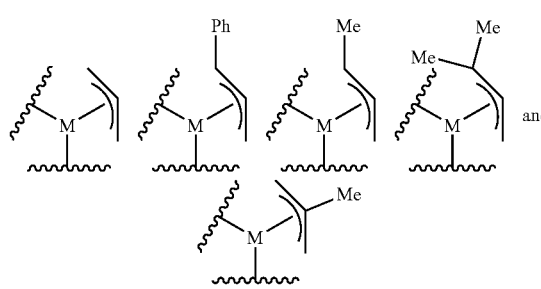

In the complex of formula (1), X is an anionic ligand. In one embodiment, X is a halo group, preferably, Cl, Br, I, and more preferably, Cl.

In one embodiment, the complex of formula (1) is a complex of formula (1a):

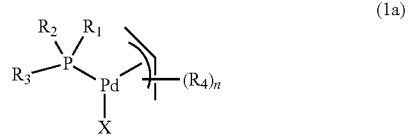

(1a)

wherein, $R_1$ and $R_2$ are independently organic groups having 1-20 carbon atoms, or $R_1$ and $R_2$ are linked to form a ring structure with the phosphorus atom, $R_3$ is selected from the group consisting of substituted and unsubstituted aryl, and substituted and unsubstituted heteroaryl, $R_4$ is an organic group having 1-20 carbon atoms, preferably substituted or unsubstituted aryl, or substituted or unsubstituted heteroaryl wherein the heteroatoms are selected from sulphur, nitrogen and oxygen, n is 0, 1, 2, 3, 4 or 5, preferably 1, 2, 3, 4 or 5, X is an anionic ligand.

$R_1$, $R_2$, $R_3$, $R_4$, n and X are as described above.

In another embodiment, the complex of formula (1) is a complex of formula (1b):

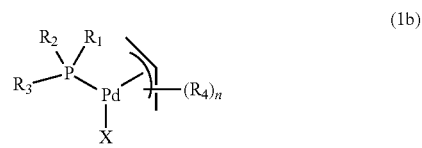

(1b)

wherein, $R_1$ and $R_2$ are independently organic groups having 1-20 carbon atoms, or $R_1$ and $R_2$ are linked to form a ring structure with the phosphorus atom, $R_3$ is selected from the group consisting of substituted and unsubstituted metallocenyl, preferably a metallocenyl of formula (2), $R_4$ is an organic group having 1-20 carbon atoms, n is 0, 1, 2, 3, 4 or 5, X is an anionic ligand.

$R_1$, $R_2$, $R_3$, $R_4$, n and X are as described above.

Preferred complexes of formula (1) are:

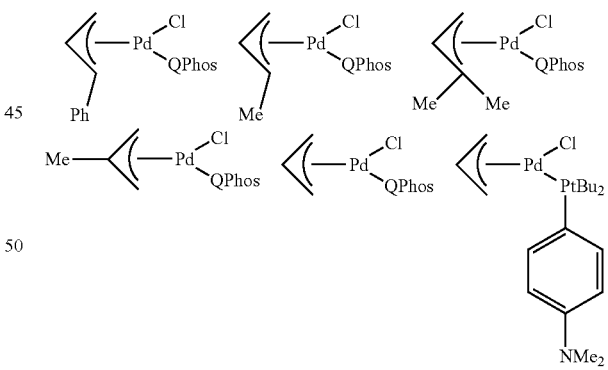

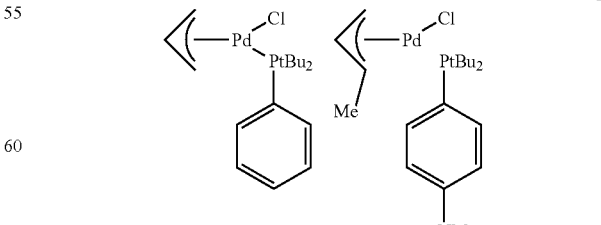

In another aspect, the present invention provides a method for the preparation of a complex of formula (1),

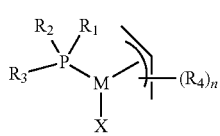
(1)

comprising the step of reacting a complex of formula (5) with $PR_1R_2R_3$,

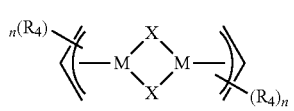
(5)

wherein,

M is palladium or nickel, $R_1$ and $R_2$ are independently organic groups having 1-20 carbon atoms, or $R_1$ and $R_2$ are linked to form a ring structure with the phosphorus atom, $R_3$ is selected from the group consisting of substituted or unsubstituted aryl, substituted or unsubstituted heteroaryl and substituted or unsubstituted metallocenyl, $R_4$ is an organic group having 1-20 carbon atoms, n is 0, 1, 2, 3, 4 or 5, X is an anionic ligand.

M, $R_1$, $R_2$, $R_3$, $R_4$, n and X are as described above.

The complex of formula (5) may be prepared according to known methods (see, for example, a) Marion, N.: Navarro, O.; Mei, J.; Stevens, E. D.; Scott, N. M.; Nolan, S. P. *J. Am. Chem. Soc.* 2006, 128, 4101. b) Auburn, P. R.; Mackenzie, P. B.; Bosnich, B. *J. Am. Chem. Soc.* 1985, 107, 2033. c) Dent, W. I.; Long, R.; Wilkinson, G. *J. Chem. Soc.* 1964, 1585. d) Nicholson, J. K.; Powell, J.; Shaw, B. L. *J. Chem. Soc.; Chem. Commun.* 1966, 174) each of which is incorporated herein by reference in its entirety for all purposes. Suitable complexes of formula (5) include:

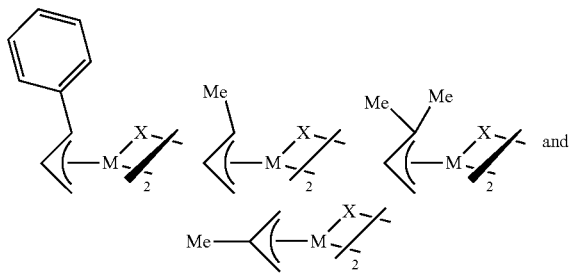

In one embodiment, the complexes of formula (5) include:

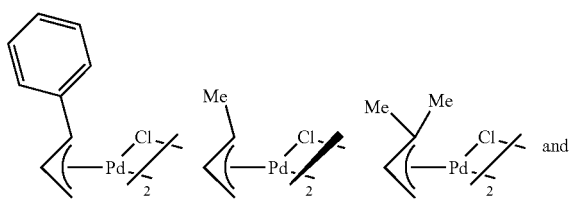

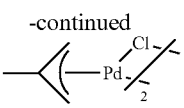

The complex of formula (5) and $PR_1R_2R_3$ may be combined in a solvent. In this case, the solvent is any suitable aprotic solvent or combination of aprotic solvents. Examples of aprotic solvents are toluene, benzene, tetrahydrofuran (THF), dichloromethane (DCM), dioxane, acetone, acetonitrile, dimethylformamide (DMF), N-methylpyrrolidine (NMP), dimethylacetamide (DMAc), methyltertbutylether (MTBE), diethylether, hexane, heptane, pentane or ethylacetate. Preferred solvents are THF, toluene, DCM or a combination thereof. The concentration of the complex of formula (5) in the solvent is preferably about 0.001 mol/L to about 0.25 mol/L and more preferably, about 0.03 mol/L to about 0.22 mol/L.

Any suitable quantity of $PR_1R_2R_3$ may be used, although it is preferred that the molar ratio of the complex of formula (5): $PR_1R_2R_3$ is from about 1:2.0 to about 1:2.2. If desired $PR_1R_2R_3$ may be used in the form of a salt, for example, a tetrafluoroborate salt.

The reaction is preferably carried out under an inert atmosphere, such as nitrogen or argon.

The process of the invention may be carried out at a temperature in the range of about −10° C. to about 60° C., preferably about 0° C. to about 35° C. and more preferably at about room temperature (i.e. about 20° C. to about 30° C.). It is preferred that the temperature is maintained below the decomposition temperature and so when the complexes of formula (5) or (1) are known to decompose within the temperature ranges given above, the temperature should be maintained below the decomposition temperature.

The reaction may be carried out for a period of from about several minutes to about 24 hours. Usually the reaction is complete in about 18 hours. On completion, a proportion of the solvent may be evaporated if desired prior to recovery of the complex. Furthermore, if desired an anti-solvent (e.g. an alkane, such as hexane) may be used to precipitate the complex from the solvent. The complex product may be recovered directly by filtering, decanting or centrifuging.

Howsoever the complex is recovered, the separated complex may be washed and then dried. Drying may be performed using known methods, for example at temperatures in the range 10-60° C. and preferably 20-40° C. under 1-30 mbar vacuum for 1 hour to 5 days. If desired the complex may be recrystallised.

The catalysts of the present invention may be used for carbon-carbon coupling reactions. Examples of carbon-carbon coupling reactions include the Heck or Suzuki reactions, ketone α-arylation reactions and aldehyde α-arylation reactions. The catalysts of the present invention may also be used for carbon-nitrogen coupling reactions, such as the Hartwig-Buckwald reaction.

In certain embodiments, the π-allyl complexes are highly active catalysts. In certain embodiments, the π-allyl complexes are stable to air and moisture at ambient temperatures. In one preferred embodiment, the π-allyl complexes Pd(π-allyl)QPhosCl and Pd(π-1-crotyl)QPhosCl exhibit high activity and/or stability to air and moisture at ambient temperatures. In particular, Pd(π-crotyl)QPhosCl has been identified as being a highly active, air-stable catalyst in Pd-catalysed C—N bond formations involving primary and secondary amines, with low catalyst loadings, short reaction times, using aryl and heteroaryl halides ranging from iodides to chlorides.

EXAMPLES

All solvents and reagents were purchased from commercial sources and used as received. All catalysts, ligands or precious metal precursors were obtained from Johnson Matthey Catalysis or Alfa Aesar. Flash chromatography was performed on a Flashmaster Personal (Biotage) using prepacked ISOLUTE silica gel cartridges. $^1$H and $^{13}$C NMR spectra were recorded on a Bruker 400 MHz spectrometer at ambient temperature in CDCl$_3$ or C$_6$D$_6$ (Sigma Aldrich). All reactions were carried out in individual Schlenk tubes under a nitrogen atmosphere. The purity of the isolated products was >95% as determined by $^1$H NMR, GC/MS or elemental analysis.

Example 1

General Procedure for the Preparation of [Pd(Optionally Substituted (R$_4$)$_n$-allyl)(X)]$_2$ Complexes Distilled H$_2$O in a three-necked roundbottom flask was purged with nitrogen for 30 minutes. PdCl$_2$ and KCl were subsequently added to the flask and the solution was stirred at room temperature for 1 h. Then, optionally substituted (R$_4$)$_n$-allyl chloride was added and the resulting reaction mixture stirred at room temperature overnight (18-20 hrs). The reaction was extracted with chloroform, and the aqueous layer washed with chloroform three times. The organic layers were combined, dried over MgSO$_4$, filtered and concentrated in vacuo. The crude product was recrystallised from chloroform and methyl tert-butyl ether, and the resulting solid was isolated by filtration and dried in vacuo.

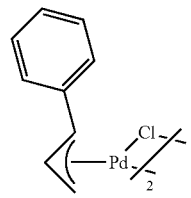

[Pd(π-cinnamyl)Cl]$_2$

PdCl$_2$ (590 mg, 3.33 mmol); KCl (473 mg, 6.67 mmol); cinnamyl chloride (1.39 mL, 9.99 mmol); H$_2$O (83 mL). The dimer was obtained as a yellow solid (494 mg, 58%).

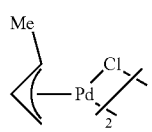

[Pd(π-1-crotyl)Cl]$_2$

PdCl$_2$ (590 mg, 3.33 mmol); KCl (473 mg, 6.67 mmol); crotyl chloride (0.97 mL, 9.99 mmol); H$_2$O (83 mL). The dimer was obtained as a yellow solid (636 mg, 97%).

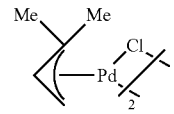

[Pd(π-prenyl)Cl]$_2$

PdCl$_2$ (590 mg, 3.33 mmol); KCl (473 mg, 6.67 mmol); 1-chloride-3-methyl-2-butene (1.13 mL, 9.99 mmol); H$_2$O (83 mL). The dimer was obtained as a yellow solid (606 mg, 87%).

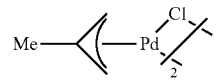

[Pd(π-prenyl)Cl]$_2$

PdCl$_2$ (590 mg, 3.33 mmol); KCl (473 mg, 6.67 mmol); 3-chloride-2-methyl-1-propene (0.98 mL, 9.99 mmol); H$_2$O (83 mL). The dimer was obtained as a yellow solid (269 mg, 41%).

General Procedure for the Preparation of Pd(π-Optionally Substituted (R$_4$)$_n$-allyl)(PR$_1$R$_2$R$_3$)(X) Complexes:

The [Pd(π-optionally substituted (R$_4$)$_n$-allyl)Cl]$_2$ and the PR$_1$R$_2$R$_3$ ligand were put in a Schlenk flask. The flask was evacuated and backfilled with nitrogen three times, then the solvent was added. The reaction mixture was stirred at room temperature for the indicated time and then the solvent was removed in vacuo. The resulting solid was triturated with anhydrous hexane and the solid isolated by filtration and dried in vacuo to give the desired palladium complex. The structures of the various complexes prepared in this manner may be represented as follows:

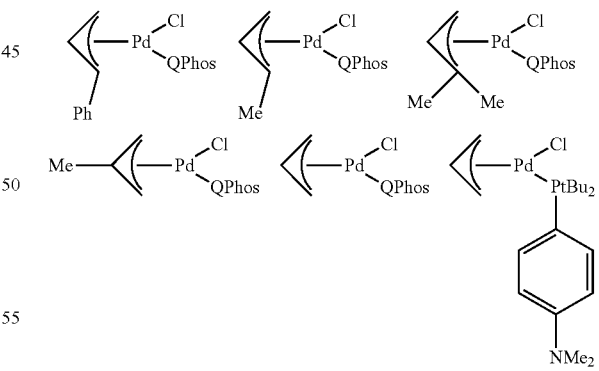

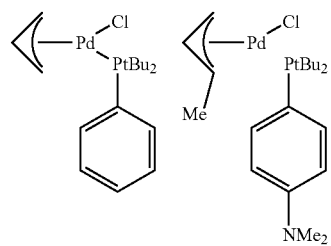

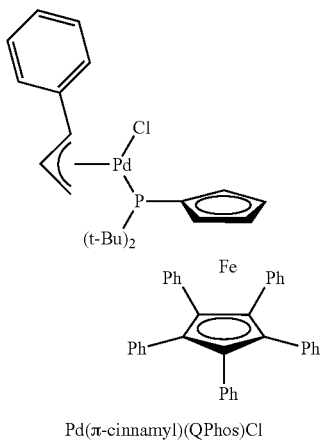

Pd(π-cinnamyl)(QPhos)Cl

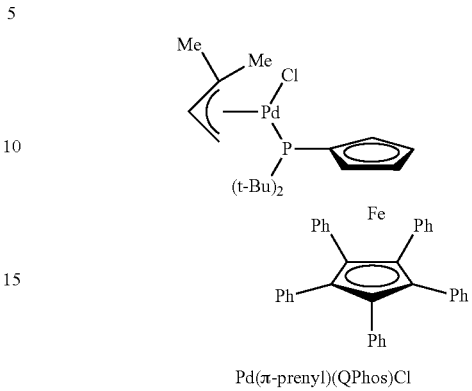

Pd(π-prenyl)(QPhos)Cl

[Pd(π-cinnamyl)Cl]$_2$ (74 mg, 0.14 mmol); QPhos (223 mg, 0.31 mmol); THF (2.8 mL); 18 hrs. Product obtained as a pink solid (233 mg, 86%); $^1$H NMR (CDCl$_3$, 400 MHz): δ 7.48-7.46 (m, 2H, CH$_2$=CH—CH—C$_6$H$_5$), 7.37-7.35 (m, 3H, 2=CH—CH—C$_6$H$_5$), 7.14-7.03 (m, 25H, H—Ar), 5.68-5.60 (m, 1H, CH$_2$=CH—CH—C$_6$H$_5$), 5.20 (dd, J 13.2, 9.6, 1H, CH$_2$=CH—CH—C$_6$H$_5$), 5.08 (br s, 1H, Cp-H), 4.84-4.81 (m, 1H, Cp-H), 4.53 (app. s, 2H, Cp-H), 4.02 (br s, 1H, CH$_2$=CH—CH—C$_6$H$_5$), 2.79 (br s, 1H, CH$_2$=CH—CH—C$_6$H$_5$), 1.27-1.07 (m, 18H, PC(CH$_3$)$_3$); $^{13}$C (CDCl$_3$, 100 MHz): δ 136.4, 135.1, 132.6, 128.6, 128.3, 127.4, 126.5, 107.3, 87.7, 68.0, 53.9, 30.7; $^{31}$P NMR (CDCl$_3$, 162 MHz): δ 67.4. Elemental analysis, found: C 70.39, H 5.93, Cl 3.52, P 3.18 (theoretical C 70.60, H 5.82, Cl 3.66, P 3.19).

Single crystals of Pd(cinnamyl)QPhosCl were obtained by slow diffusion of 40-60 petroleum ether into a CH$_2$Cl$_2$ solution, respectively, at −18° C. (see FIG. 1).

Figure 2:
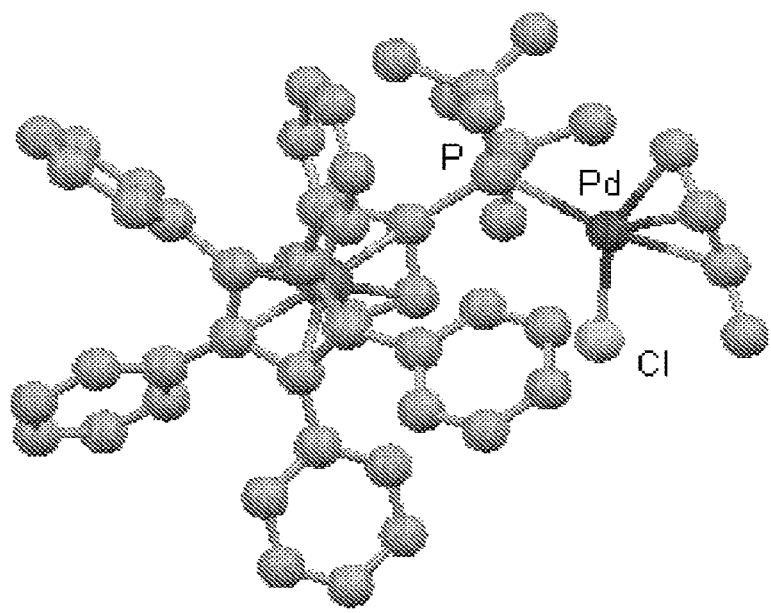
FIG. 2 is an X-ray crystal structure of Pd(π-crotyl) QPhosCl

Single crystals of Pd(π-crotyl)QPhosCl were obtained by slow diffusion of 40-60 petroleum ether into an EtOAc solution at −18° C. (see FIG. 2).

[Pd(π-prenyl)Cl]$_2$ (200 mg, 0.48 mmol); QPhos (751 mg, 1.06 mmol); THF (10 mL); 18 hrs. Product obtained as a pink solid (867 mg, 98%); $^1$H NMR (CDCl$_3$, 400 MHz): δ 7.19-7.04 (m, 25H, C$_6$H$_5$), 5.44 (br s, 1H, Cp-H), 4.94-4.81 (m, 2H, CH$_2$=CH(CH$_3$)$_2$, Cp-H), 4.51 (s, 2H, Cp-H), 3.52 (d, J 6.8, 1H CH$_2$=CH (CH$_3$)$_2$), 2.71 (d, J 12.0, CH$_2$=CH—(CH$_3$)$_2$), 1.80 (d, J 8.4, 3H, CH$_2$=CH—(CH$_3$)$_2$), 1.62 (t, J 7.2, 3H, CH$_2$=CH—(CH$_3$)$_2$), 1.24 (d, J 14.4, 9H, PC(CH$_3$)$_3$), 1.15 (d, J 14.4, 9H, PC(CH$_3$)$_3$); $^{13}$0 (CDCl$_3$, 100 MHz): δ 135.2, 132.6, 127.3, 126.5, 121.2, 106.8, 87.7, 80.3, 47.4, 37.8, 30.9, 30.6; $^{31}$P NMR (CDCl$_3$, 162 MHz): δ 68.3. Elemental analysis, found: C 68.81, H 6.44, Cl 4.57, P 3.25 (theoretical C 69.06, H 6.12, Cl 3.85, P 3.36).

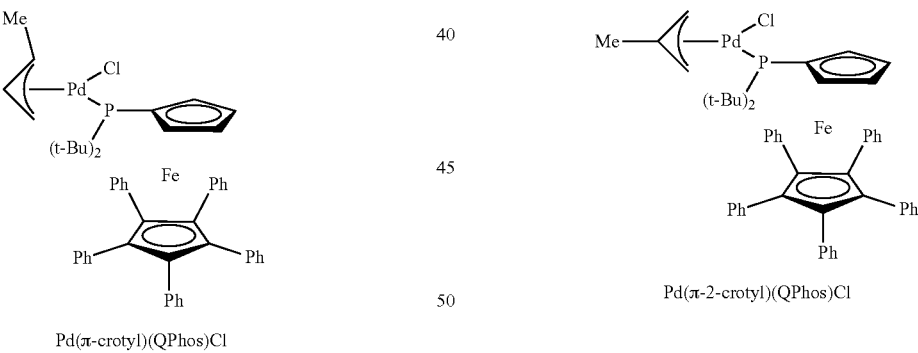

Pd(π-crotyl)(QPhos)Cl

Pd(π-2-crotyl)(QPhos)Cl

[Pd(π-crotyl)Cl]$_2$ (200 mg, 0.51 mmol); QPhos (798 mg, 1.12 mmol); THF (10 mL); 18 hrs. The complex was obtained as a pink solid (891 mg, 96%); $^1$H NMR (CDCl$_3$, 400 MHz): δ 7.15-7.03 (m, 25H, H—Ar), 5.34 (br s, 1H, Cp-H), 5.09-5.00 (m, 2H, CH$_2$=CH—CH—CH$_3$, Cp-H), 4.54-4.53 (m, 2H, Cp-H), 4.49-4.39 (m, 1H, CH$_2$=CH—CH—CH$_3$), 3.77 (d, J 6.4, 1H, CH$_2$=CH—CH—CH$_3$), 2.54 (d, J 11.6, 1H, CH$_2$=CH—CH—CH$_3$), 1.74 (dd, J 8.4, 6.8, 3H, CH$_2$=CH—CH—CH$_3$), 1.17 (t, J 13.2, 18H, PC(CH$_3$)$_3$); $^{13}$C (CDCl$_3$, 100 MHz): δ 135.2, 132.6, 127.3, 126.5, 113.2, 103.0, 87.7, 80.8, 80.1, 52.2, 37.8, 30.6; $^{31}$P NMR (CDCl$_3$, 162 MHz): δ 65.0. Elemental analysis, found: C 68.90, H 6.16, Cl 3.77, P 3.40 (theoretical: C 68.81, H 6.00, 013.91, P 3.41).

[Pd(π-2-crotyl)Cl]$_2$ (200 mg, 0.51 mmol); QPhos (798 mg, 1.12 mmol); THF (5 mL); 18 hrs. The complex was obtained as a pink solid (788 mg, 85%); $^1$H NMR (CDCl$_3$, 400 MHz): δ 7.19-6.98 (m, 25H, H—Ar), 5.27 (br s, 1 H, Cp-H), 4.93 (br s, 1 H, Cp-H), 4.65 (dd, J 6.4, 2.8, 1 H, CH$_2$=C(CH$_3$)—CH$_2$), 4.55 (br s, 2H, Cp-H), 3.84 (d, J 2.8, 1 H, CH$_2$=C(CH$_3$)—CH$_2$), 3.77 (d, J 8.4, 1H, CH$_2$=C (CH$_3$)—CH$_2$), 2.68 (s, 1H, CH$_2$=C(CH$_3$)—CH$_2$), 1.94 (s, 3H, CH$_2$=C(CH$_3$)—CH$_2$), 1.18 (d, J 14.0, 9H, PC(CH$_3$)$_3$), 1.13 (d, J 14.0, 9H, PC(CH$_3$)$_3$); $^{13}$C (CDCl$_3$, 100 MHz): δ 134.5, 131.9, 128.6, 126.7, 126.6, 125.9, 87.1, 79.4, 57.2, 30.0, 29.9, 29.6, 29.5, 21.8; $^{31}$P NMR (CDCl$_3$, 162 MHz): δ 62.0. Elemental analysis, found: C 69.59, H 6.23, Cl 3.41, P 3.42 (theoretical C 68.81, H 6.00, Cl 3.91, P 3.41).

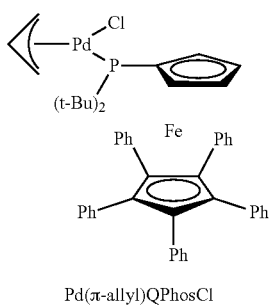

Pd(π-allyl)QPhosCl

[Pd(π-allyl)Cl]₂ (2.0 mmol); QPhos (4.4 mmol); THF (45 mL); 18 hrs. The product was obtained as a pink solid (3.2 g, 90%); ¹H NMR (CDCl₃, 400 MHz): δ 7.17-7.01 (m, 25H, C₆H₅), 5.46-5.36 (m, 1H, CH₂=CH—CH₂), 5.33 (br s, 1H, Fe—H), 5.08 (br s, 1H, Fe—H), 4.83 (t, J 6.8, 1H, CH₂=CH—CH₂), 4.56 (br s, 1H, Fe—H), 4.54 (br s, 1H, Fe—H), 4.04 (d, J 4.8, 1H, CH₂=CH—CH₂), 3.87 (dd, J 13.6, 8.4, CH₂=CH—CH₂), 2.78 (d, J 12.4, 2H, CH₂=CH—CH₂), 1.17 (d, J 14.0, PC(CH₃)₃); ¹³C (CDCl₃, 100 MHz): δ 135.2, 132.7, 132.5, 132.1, 127.3, 126.5, 114.2, 87.8, 83.5, 79.7, 67.1, 57.5, 37.8, 30.5; ³¹P NMR (CDCl₃, 162 MHz): δ 61.8. Elemental analysis, found: C 68.40, H 6.00, Cl 3.83, P 3.42 (theoretical C 68.54, H 5.87, Cl 3.97, P 3.47).

Figure 3:
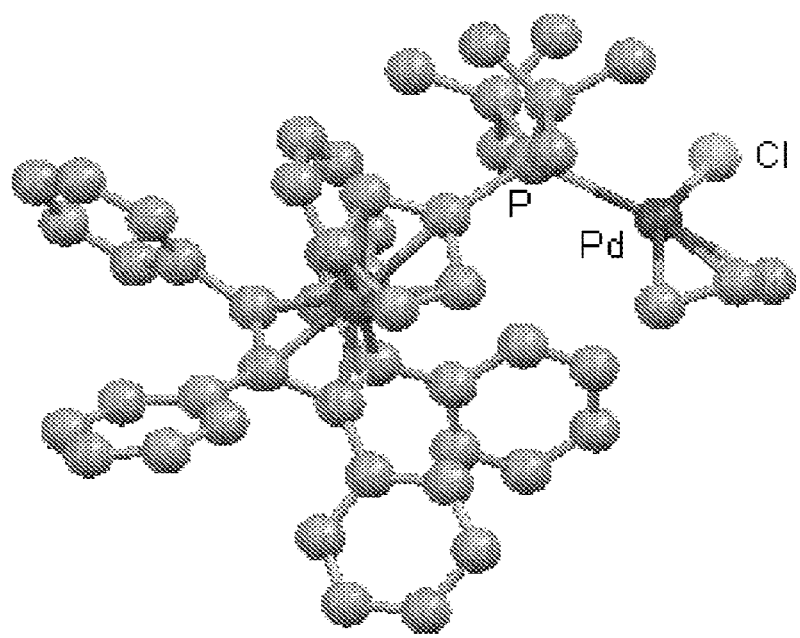
FIG. 3 is an X-ray crystal structure of Pd(π-allyl)QPhosCl.

Single crystals of Pd(π-allyl)QPhosCl were obtained by slow diffusion of diethyl ether into a CH₂Cl₂ solution (see FIG. 3).

The X-ray structures of Pd(π-allyl)QPhosCl and Pd(π-crotyl)QPhosCl (see FIG. 2) are different in terms of the opposite orientation of the halide, presumably due to the steric effect of the Me group on the 3-position of the allyl in Pd(π-crotyl)QPhosCl.

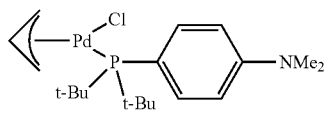

Pd(π-allyl)(Amphos)Cl

[Pd(π-allyl)Cl]₂ (311 mg, 0.85 mmol); Amphos (496 mg, 1.87 mmol); THF (17 mL); 18 hrs. Product obtained as a yellow solid (727 mg, 96%); ¹H NMR (CDCl₃, 400 MHz): δ 7.50 (app. t, J 8.8, 2H, H—Ar), 6.65 (d, J 8.0, 2H, H—Ar), 5.50 (heptet, J 7.2, 1 H, CH₂=CH—CH₂), 4.63 (dt, J 6.8, 2.0, 1 H, CH₂=CH—CH₂), 3.69 (dd, J 13.2, 9.2,1 H, CH₂=CH—CH₂), 3.39 (d, J 6.0, 1H, CH₂=CH—CH₂), 3.01 (s, 6H, N(CH₃)₂), 2.68 (d, J 12.0, 1H CH₂=CH—CH₂), 1.47 (d, J 14.0, 9H, PC(CH₃)₃), 1.39 (d, J 14.0, 9H, PC(CH₃)₃); ¹³0 (CDCl₃, 100 MHz): δ 150.9, 136.7, 136.6, 116.9, 116.6, 115.2, 110.4, 110.3, 80.7, 80.4, 58.8, 39.9, 36.0, 30.6, 29.9; ³¹P NMR (CDCl3, 162 MHz): δ 61.9. Elemental analysis, found: C 51.44, H 7.51, Cl 7.54, P 6.94 (theoretical C 50.90, H 7.42, Cl 7.91, P 6.91).

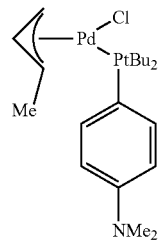

Pd(π-crotyl)(Amphos)Cl

[Pd(crotyl)Cl]₂ (132 mg, 0.34 mmol); P(t-Bu)₂(p-NMe₂C₆H₄) (180 mg, 0.68 mmol); THF (3.7 mL); 90 min. Product obtained as a yellow solid (263 mg, 85%); ¹H NMR (CDCl₃, 400 MHz): δ 7.52 (t, J 8.8, 2H), 6.65 (d, J 8.0, 2H), 5.25-5.17 (m, 1H), 4.40-4.29 (m, 1H), 3.21-3.19 (m, 1H), 3.00 (s, 3H), 2.47 (d, J 11.6, 1H), 1.77 (dd, J 8.4, 6.4, 3H), 1.44 (d, J 13.6, 9H), 1.38 (d, J 13.6, 9H); ¹³C (CDCl₃, 100 MHz): δ 150.9, 149.6, 136.9, 136.7, 117.1, 116.8, 114.1, 110.3, 99.8, 99.6, 53.5, 40.0, 35.8, 30.6, 29.9, 17.4; ³¹P NMR (CDCl₃, 162 MHz): δ 65.5; Elemental analysis, found: C 51.93, H 7.54, N 2.84, P 6.58. (theoretical C 51.96, H 7.63, N 3.03, P 6.70).

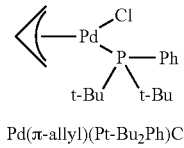

Pd(π-allyl)(Pt-Bu₂Ph)Cl

[Pd(π-allyl)Cl]₂ (100 mg, 0.27 mmol); Pt—Bu₂Ph.HBF4 (169 mg, 0.55 mmol); toluene (1.5 mL), 18 hrs. The product was obtained as a yellow solid (217 mg, 98%); ¹H NMR (CDCl₃, 400 MHz): δ 7.90-7.68 (m, 5H, H—Ar), 5.51-5.42 (m, 1H, CH₂=CH—CH₂), 4.12 (d, J 6.4, 2H, CH₂=CH—CH₂), 3.05 (d, J 12.0, 2H, CH₂=CH—CH₂), 1.55 (d, J 16.8, PPh(CH₃)₂); ¹³C (CDCl₃, 100 MHz): δ 135.0, 130.5, 127.4, 116.0, 115.3, 111.2, 63.0, 34.4, 28.0; ³¹P NMR (CDCl₃, 162 MHz): δ 44.4.

Example 2

General Procedure for the Buchwald-Hartwig Coupling Reaction

A Schlenk flask was charged with the catalyst, NaOtBu and aryl halide, if solid, and the flask was evacuated and backfilled with nitrogen three times. Subsequently, a solution of the aryl halide, if liquid, and the amine in toluene was added. The resulting reaction mixture was stirred under nitrogen at the indicated temperature for the indicated time, then the mixture was absorbed onto silica gel and purified by flash column chromatography (EtOAc/40-60 petroleum ether eluent).

The relative activities of Pd(π-allyl)QPhosCl and Pd(π-crotyl)QPhosCl were explored in a model C—N coupling reaction of 4-bromoanisole with N-methylaniline at room temperature (see Tables 1 and 2).

TABLE 1

Optimization and Activities of Pd(π-allyl)QPhosCl and Pd(π-crotyl)QPhosCl.[a]

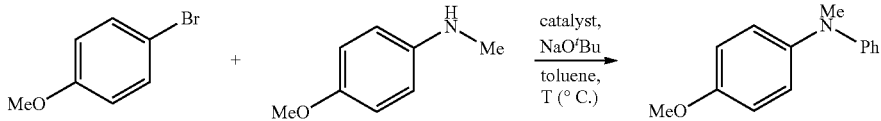 [SMILES: COc1ccc(Br)cc1 ; CNc1ccc(OC)cc1 ; COc1ccc(N(C)c2ccccc2)cc1]

| catalyst | toluene (mL) | T (° C.) | time (hrs) | conversion[b] (%) |
|---|---|---|---|---|
| Pd(π-allyl)QphosCl (1.0 mol %) | 4.0 | 25 | 6 | 97 |
| Pd(π-crotyl)QPhosCl (1.0 mol %) | 4.0 | 25 | 3 | 100 |
| Pd(π-allyl)QPhosCl (0.5 mol %) | 4.0 | 25 | 23 | 54 |
| Pd(π-crotyl)QPhosCl (0.5 mol %) | 4.0 | 25 | 5 | 100 |
| Pd(π-allyl)QPhosCl (0.5 mol %) | 2.0 | 25 | 7 | 93 |
| Pd(π-crotyl)QPhosCl (0.5 mol %) | 2.0 | 25 | 1 | 100 |

[a]4-bromoanisole (1.6 mmol), N-methylaniline (2.0 mmol), NaOt-Bu (2.4 mmol) [b]GC/MS conversion.

Pd(allyl)QPhosCl on comparision with Pd(π-1-crotyl) QPhosCl at a lower concentration (0.5 mol %) gave 54% conversion after 23 hours vs 100% at 5 hours of reaction time. However, by keeping the catalyst loadings of Pd(allyl) QPhosCL at 0.5 mol % while increasing the concentration from 0.4 to 0.8M, 93% conversion was observed within 7 hours. The catalyst Pd(π-1-crotyl)QPhosCl gave 100% conversion to the product after 1 hour, demonstrating its superiority.

TABLE 2

Comparison of the Relative Activities of Pd(π-allyl)QPhosCl and Pd(π-crotyl)QPhosCl.[a]

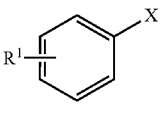

| Ar—X | amine | T (° C.) | catalyst | time (hrs) | conversion[b] (%) |
|---|---|---|---|---|---|
| 2-Me-C₆H₄Br | 2,6-iPr₂-C₆H₃NH₂ | 50 | Pd(π-allyl)QPhosCl | 6.5 | 97 |
|  |  | 50 | Pd(π-crotyl)QPhosCl | 2 | 100 |
| 4-OMe-C₆H₄Cl | 2,6-iPr₂-C₆H₃NH₂ | 100 | Pd(π-allyl)QPhosCl | 0.6 | 99 |
|  |  | 100 | Pd(π-crotyl)QPhosCl | 0.6 | 99 |

[a]aryl halide (1.6 mmol), amine (2.0 mmol), NaOt-Bu (2.4 mmol), toluene (2.0 mL) [b]GC/MS conversion.

Example 3

General Procedure for the Buchwald-Hartwig Coupling Reaction

A Schlenk flask was charged with the catalyst, NaOtBu and aryl halide, if solid, and the flask was evacuated and backfilled with nitrogen three times. Subsequently, a solution of the aryl halide, if liquid, and the amine in toluene was added. The resulting reaction mixture was stirred under nitrogen at the indicated temperature for the indicated time, then the mixture was absorbed onto silica gel and purified by flash column chromatography (EtOAc/40-60 petroleum ether eluent).

TABLE 3

Reaction of 4-bromoanisole and N-methylaniline with various complexes

| catalyst (mol %) | T (° C.) | time (hrs) | Conversion[a] (%) |
|---|---|---|---|
| Pd(allyl)QPhosCl (1.0) | 25 | 6 | 97 (96) |
| Pd(allyl)P$^t$Bu$_2$PhCl (1.0) | 25 | 22 | 8 (8) |
| Pd(allyl)AmPhosCl (1.0) | 25 | 22 | 18 |
| Pd(1-crotyl)AmPhosCl (1.0) | 25 | 22 | 95 |
| Pd(prenyl)QPhosCl (1.0) | 25 | 6 | 100 (99) |
| Pd(prenyl)QPhosCl (0.5) | 25 | 22 | 100 |
| Pd(cinnamyl)QPhosCl (1.0) | 25 | 22 | 81 (66) |
| Pd(1-crotyl)QPhosCl (1.0) | 25 | 3 | 100 (99) |
| Pd(1-crotyl)QPhosCl (0.5) | 25 | 18 | 99 |
| Pd(1-crotyl)QPhosCl (0.1) | 25 | 18 | 95 |
| Pd(2-crotyl)QPhosCl (1.0) | 25 | 18 | 62 |

[a]GC/MS conversion. Isolated yield in parentheses

In order to get an idea of the relative activities of the present catalysts, a C—N coupling reaction of 4-bromoanisole with N-methylaniline at room temperature was carried out. At 1 mol % palladium loading, the Q-Phos based catalysts Pd(π-allyl)QPhosCl, Pd(π-1-crotyl)QPhosCl and Pd(π-prenyl)QPhosCl all provided the product with conversions greater than 90% within 3-18 hours. The Pd(crotyl) QPhosCl complex gave the desired product in the highest conversion even at 0.1 mol % palladium loading, while Pd(π-prenyl)QPhosCl gave the second highest activity. Pd(π-1-crotyl)AmphosCl resulted in 95% conversion to the product with 22 hours of reaction time.

Example 4

Comparison of In Situ and Commercially Available Catalysts in C—N Coupling

A comparison of in situ and commercially available catalysts and catalytic systems in a C—N coupling reaction was carried out. In this reaction, N-methylaniline was coupled with 4-bromoanisole to give N-(4-bromophenyl)-N-methyl-phenylamine under the conditions set out in Table 4.

TABLE 4

Reaction of 4-bromoanisole and N-methylaniline

| substrates[a] | catalyst (mol %) | T (° C.) | time (hrs) | Conversion[b] (%) |
|---|---|---|---|---|
| | Pd(π-1-crotyl)QPhosCl (1.0) | 25 | 3 | 100 |
| | Pd(π-1-crotyl)QPhosCl (0.5) | 25 | 18 | 99[c] |
| | Pd(π-1-crotyl)QPhosCl (0.1) | 25 | 18 | 95 |
| | Pd(π-allyl)QPhosCl (1.0) | 25 | 6 | 97 |
| | Pd$_2$(dba)$_3$ (0.25) QPhos (0.5) | 25 | 21 | 53 |
| | Pd-113 (0.25)[d] | 25 | 3 | 80 |
| | Pd-116 (0.5)[e] | 25 | 23 | 55 |
| | Nolan's cat. (0.5) | 25 | 21 | 0 |
| | Pd(OAc)$_2$ (0.5) XPhos (0.5)[f] | 25 | 21 | 0 |
| | Pd(OAc)$_2$ (0.5) QPhos (0.5) | 25 | 23 | 0 |

[a]amine (1.0 mmol), aryl halide (0.8 mmol), NaOtBu (1.2 mmol), toluene (2.0 mL) [b]GC/MS conversions [c]Average of three reactions [d]Pd-113 = [Pd(μ-Br) $^t$-Bu$_3$P)$_2$] [e]Pd-116 = $^t$Bu$_3$P-Pd-P$^t$Bu$_3$ [f]XPhos = 2',4'6'-triisopropylbiphenyl-2-dichlorohexylphosphine

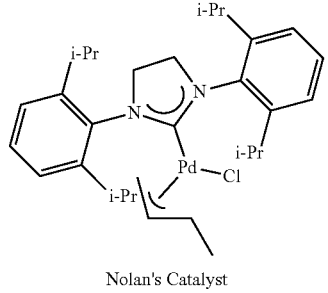

Nolan's Catalyst

The Pd(1-crotyl)QPhos complex showed a superior activity to the other catalytic systems with a 99% conversion at 0.5 mol % catalyst loading and a 95% conversion at 0.1 mol % loading. The Pd(allyl)QPhosCl complex also provided the desired product with a good conversion.

Pd-113 showed good activity, however, the conversion in this case was lower than that of Pd(1-crotyl)QPhos and Pd(allyl)QPhosCl. In addition, Pd-113 is air- and moisture sensitive and has to be stored under a nitrogen atmosphere.

Example 5

Substrate Scope of C—N Coupling

General Procedure for the Buchwald-Hartwig Coupling Reaction

A Schlenk flask was charged with the catalyst, NaOt-Bu and aryl halide, if solid, and the flask was evacuated and backfilled with nitrogen three times. Subsequently, a solution of the aryl halide, if liquid, and the amine in toluene was added. The resulting reaction mixture was stirred under nitrogen at the indicated temperature and time (see Tables in communication). The crude mixture was absorbed onto silica gel (Merck Silica Gel 60 (0.040-0.063 mm)) and purified by flash column chromatography (MTBE/40-60 petroleum ether eluent).

TABLE 5

C—N Bond Formation Mediated by 0.5 mol % Pd(crotyl)QPhosCl[a]

$$\text{R}^1\text{-C}_6\text{H}_4\text{-X} + \text{R}^2\text{-C}_6\text{H}_4\text{-NHR} \xrightarrow[\text{toluene (2.0 mL), T °C}]{\text{0.5 mol % Pd(crotyl)QPhosCl, NaO}^t\text{Bu}} \text{R}^1\text{-C}_6\text{H}_4\text{-NR-C}_6\text{H}_4\text{-R}^2$$

| Ar—X | amine | X | T (°C.) | time (h) | product | yield (%) |
|---|---|---|---|---|---|---|
| 3,4,5-trimethoxyphenyl-X | methyl 2-aminobenzoate | Br | 110 | 20 | (coupled product) | 65[b] |
| 4-MeO-C₆H₄-X | 2,6-diisopropylaniline | Br / Cl | 25 / 100 | 1.5 / 0.5 | (coupled product) | 96[c] / 95 |
| 4-MeO-C₆H₄-X | morpholine | Br / Cl | 50 / 100 | 16 / 2.5 | 4-(4-methoxyphenyl)morpholine | 98 / 96 |
| 4-MeO-C₆H₄-X | NHPh₂ | Br / Cl | 25 / 100 | 3 / 3 | 4-methoxy-N,N-diphenylaniline | 84[d] / 68[d] |
| 4-MeO-C₆H₄-X | aniline | Br | 50 | 2 | 3-methoxy-N-phenylaniline | 91 |

TABLE 5-continued

C—N Bond Formation Mediated by 0.5 mol % Pd(crotyl)QPhosCl[a]

| Ar—X | amine | X | T (° C.) | time (h) | product | yield (%) |
|---|---|---|---|---|---|---|
| 4-MeO-C6H4-X | PhNHMe | Br | 25 | 1 | 4-MeO-C6H4-N(Me)Ph | 93 |
|  |  | Cl | 100 | 1 |  | 98 |
|  |  | I | 25 | 16 |  | 95[e] |
| 4-Cl-2-Me-C6H3-X | PhNHMe | Br | 50 | 3 | 4-Cl-2-Me-C6H3-N(Me)Ph | 88 |
| 3-Cl-4-Me-C6H3-X | PhNHMe | Br | 25 | 1 | 3-Cl-4-Me-C6H3-N(Me)Ph | 97 |
| 2-Me-C6H4-X | 2,6-iPr2-C6H3-NH2 | Br | 50 | 2.5 | 2-Me-C6H4-NH-(2,6-iPr2-C6H3) | 96 |
|  |  | Cl | 100 | 21 |  | 87[f] |
| 2-Me-C6H4-X | PhNH2 | Br | 50 | 22 | 2-Me-C6H4-NHPh | 91 |
|  |  | Cl | 100 | 2.5 |  | 83 |
| 3-MeO-C6H4-X | PhNH2 | Cl | 80 | 3 | 3-MeO-C6H4-NHPh | 91[e] |
| 4-NC-C6H4-X | PhNH2 | Br | 80 | 4 | 4-NC-C6H4-NHPh | 93[e] |
| 4-Me-C6H4-X | PhNHMe | Br | 100 | 1 | 4-Me-C6H4-NHPh | 83[g] |
|  |  | Cl | 100 | 1 |  | 92[h] |

TABLE 5-continued

C—N Bond Formation Mediated by 0.5 mol % Pd(crotyl)QPhosCl[a]

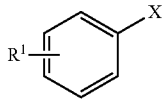

| Ar—X | amine | X | T (°C.) | time (h) | product | yield (%) |
|---|---|---|---|---|---|---|
| 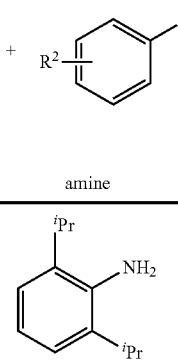 | 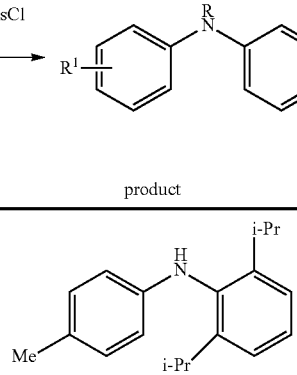 | Br | 100 | 2 | 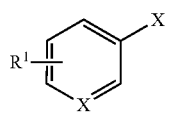 | 91[g] |

[a]aryl halide (1.6 mmol), amine (2.0 mmol), NaOt-Bu (2.4 mmol), toluene (2.0 mL) [b]Using 2 mol % Pd(crotyl)QPhosCl [c]Using 1 mol % Pd(crotyl)QPhosCl [d]NMR yield of isolated mixture of excess diphenylamine and desired product [e]Unoptimized reaction time [f]GC/MS conversion [g]Using 0.05 mol % Pd(π-crotyl)QPhosCl [h]Using 0.1 mol % Pd(π-crotyl)QPhosCl.

Pd(π-crotyl)QPhosCl has been evaluated in several substrates for C—N coupling using a range of aryl halides with both primary and secondary amines (Table 5). The inventors have also demonstrated a number of examples of a chemoselective amination reaction of an aryl bromide in the presence of a chloride functionality. This was achieved by virtue of the fact that the aryl bromides required lower reaction temperatures than the aryl chlorides. In addition, Pd(π-crotyl)QPhosCl effected the amination of an aryl iodide, a substrate which has been considered to be a problematic coupling partner in Pd catalysed C—N bond formation processes.

The order of reactivity in aminations mediated by Pd(π-crotyl)QPhosCl appears to be the reverse to that observed in conventional Pd mediated coupling reactions. In this respect, electronrich aryl halides are aminated in higher yields at shorter reaction times than the electron-deficient electrophiles. Noteworthy is the amination of a very electron-rich tris-methoxybromobenzene in 65% yield.

As can be seen from Table 6, heterocyclic halides have also been successfully coupled.

TABLE 6

C—N Bond Formation using Heterocyclic Halides Mediated by 2 mol % Pd(crotyl)QPhosCl[a]

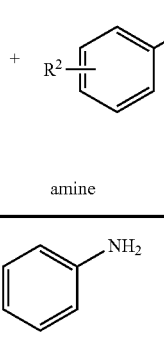

| Ar—X | amine | X | T °C. | time (h) | product | yield(%) |
|---|---|---|---|---|---|---|
| 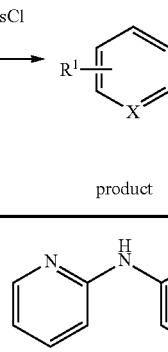 | 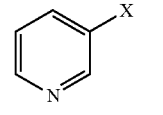 | Br<br>Cl | 100<br>100 | 3.5<br>3.5 | 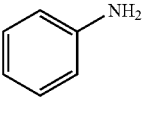 | 94<br>86 |
| 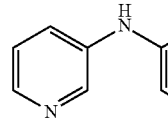 | 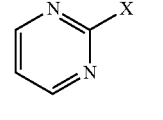 | Br<br>Cl | 100<br>100 | 2<br>2.5 | 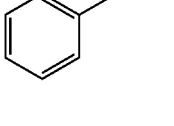 | 79<br>88 |
| 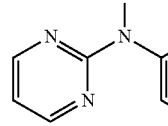 |  | Br | 50 | 3 h |  | 83 |

TABLE 6-continued

C—N Bond Formation using Heterocyclic Halides Mediated by 2 mol % Pd(crotyl)QPhosCl[a]

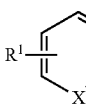

| Ar—X | amine | X | T ° C. | time (h) | product | yield(%) |
|---|---|---|---|---|---|---|
| 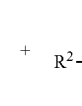 | 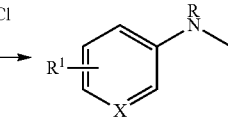 | Br<br>Br<br>Cl | 100<br>25<br>100 | 3<br>18<br>3 | 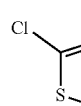 | 90<br>76[b]<br>57 |
| 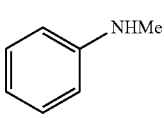 |  | Br | 25 | 20 | 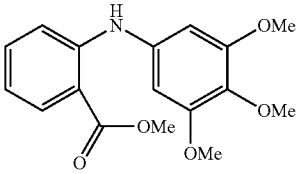 | 44 |

[a] aryl halide (1.6 mmol), amine (2.0 mmol), NaOt-Bu (2.4 mmol), toluene (2.0 mL) [b] Isolated yield using 1 mol % Pd(crotyl)QPhosCl. Unreacted aryl bromide could be detected by TLC before purification, indicating an incomplete reaction.

Pyridine-, pyrimidine- and thiophene halides gave C—N coupled products in good yields at 100° C. The reaction using 3-bromothiophene has been demonstrated at room temperature.

Experimental Data for the Products Detailed in Tables 5 and 6

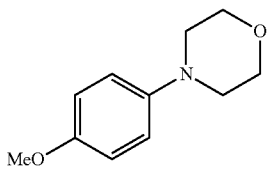

2-CO$_2$Me-3',4',5'-trimethoxy-diphenylamine

Methyl anthranilate (390 μL, 3.0 mmol); 5-bromo-1,2,3-trimethoxybenzene (594 mg, 2.3 mmol); NaOtBu (345 mg, 3.6 mmol); Pd(π-crotyl)QPhosCl (43.5 mg, 0.06 mmol, 2.0 mol %); toluene (5.0 mL). The general procedure afforded the title compound as an off-white solid (462 mg, 65%); $^1$H NMR (CDCl$_3$, 400 MHz): δ 9.39 (br s, 1H), 7.96 (dd, J 4.4, 1.6, 1H), 7.33 (dd, J 6.8, 1.6, 1H), 7.21 (d, J 8.4, 1H), 6.73 (dd, J 8.0, 0.8, 1H), 6.49 (s, 2H), 3.91 (s, 3H), 3.85 (s, 3H), 3.83 (s, 6H); $^{13}$C (CDCl$_3$, 100 MHz): δ 169.0, 153.8, 148.4, 136.6, 134.6, 134.2, 131.6, 116.9, 114.1, 111.6, 100.7, 61.0, 56.1, 51.8; Elemental analysis, found: C 64.30, H 6.06, N 4.41 (theoretical: C 64.34, H 6.03, N 4.41).

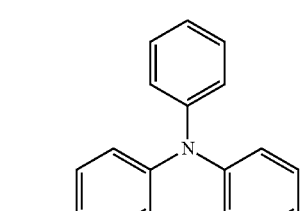

N-(2,6-diisopropylphenyl)-N-(p-methoxy)amine 4-bromoanisole (200 μL, 1.6 mmol) or 4-chloroanisole (196 μL, 1.6 mmol); 2,6-diisopropylaniline (377 μL, 2.0 mmol); NaOtBu (230 mg, 2.4 mmol); Pd(π-crotyl)QPhosCl (X=Br; 14.4 mg, 0.016 mmol, 1.0 mol %) or Pd(π-crotyl)QPhosCl (X=Cl; 7.2 mg, 0.008 mmol, 0.5 mol %); toluene (2.0 mL). The general procedure afforded the title compound in 96% yield (434 mg; X=Br) and 95% yield (429 mg; X=Cl); $^1$H NMR (CDCl$_3$, 400 MHz): δ 7.29-7.19 (m, 3H), 6.73 (d, J 6.8, 2H), 6.44 (d, J 6.8, 2H), 4.95 (br s, 1H), 3.73 (s, 3H), 3.19 (heptet, J 6.8, 2H), 1.14 (d, J 7.2, 12H); $^{13}$C (CDCl$_3$, 100 MHz): δ 152.2, 147.1, 142.2, 136.0, 126.7, 123.8, 115.0, 114.2, 55.7, 28.0, 23.8; Elemental analysis, found: C 80.95, H 9.05, N 5.03 (theoretical: C 80.52, H 8.89, N 4.94).

N-(4-methoxyphenyl)morpholine 4-bromoanisole (200 μL, 1.6 mmol) or 4-chloroanisole (196 μL, 1.6 mmol); morpholine (175 μL, 2.0 mmol); NaOtBu (230 mg, 2.4 mmol); Pd(π-crotyl)QPhosCl (7.2 mg, 0.008 mmol, 0.5 mol %); toluene (2.0 mL). The general procedure afforded the title compound in 98% yield (302 mg; X=Br) and 96% yield (297 mg; X=Cl).

N-(4-methoxyphenyl)diphenylamine 4-bromoanisole (200 μL, 1.6 mmol) or 4-chloroanisole (196 μL, 1.6 mmol); diphenylaniline (338 mg, 2.0 mmol);

NaOtBu (230 mg, 2.4 mmol); Pd(π-crotyl)QPhosCl (7.2 mg, 0.008 mmol, 0.5 mol %); toluene (2.0 mL). The general procedure afforded the title compound in 84% yield (370 mg; X=Br) and 68% yield (298 mg; X=Cl).

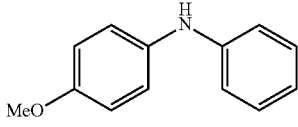

4-Methoxydiphenylamine 4-bromoanisole (200 μL, 1.6 mmol); aniline (182 μL, 2.0 mmol); NaOtBu (230 mg, 2.4 mmol); Pd(π-crotyl)QPhosCl (7.2 mg, 0.008 mmol, 0.5 mol %); toluene (2.0 mL). The general procedure afforded the title compound in 91% yield (288 mg).

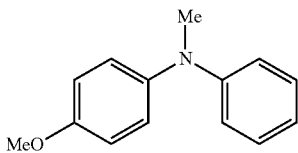

N-(4-methoxyphenyl)-N-methylaniline 4-bromoanisole (200 μL, 1.6 mmol), 4-chloroanisole (196 μL, 1.6 mmol) or 4-iodoanisole (374 mg, 1.6 mmol); N-methylaniline (217 μL, 2.0 mmol); NaOtBu (230 mg, 2.4 mmol); Pd(π-crotyl)QPhosCl (7.2 mg, 0.008 mmol, 0.5 mol %); toluene (2.0 mL). The general procedure afforded the title compound in 93% yield (315 mg; X=Br), 98% yield (335 mg; X=

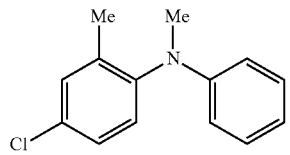

4-chloro-2-methyldiphenyl-methylamine 2-bromo-5-chlorotoluene (213 μL, 1.6 mmol); N-methylaniline (217 μL, 2.0 mmol); NaOtBu (230 mg, 2.4 mmol); Pd(π-crotyl)QPhosCl (7.2 mg, 0.008 mmol, 0.5 mol %); toluene (2.0 mL). The general procedure afforded the title compound in 88% yield (324 mg); $^1$H NMR (CDCl$_3$, 400 MHz): δ 7.27 (d, J 2.0, 1H), 7.21-7.16 (m, 3H), 7.07 (d, J 8.4, 1H), 6.73 (t, J 7.2, 1H), 6.53 (d, J 8.0, 2H), 3.19 (s, 3H), 2.11 (s, 3H); $^{13}$C (CDCl$_3$, 100 MHz) δ 146.5, 143.1, 136.4, 129.1, 128.9, 127.2, 126.7, 125.3, 114.9, 110.7, 36.8, 15.5; Elemental analysis, found: C 72.31, H 6.13, N 6.05 (theoretical: C 72.57, H 6.09, N 6.04).

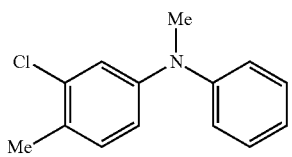

3-chloro-4-methyldiphenyl-methylamine 4-bromo-2-chlorotoluene (217 μL, 1.6 mmol); N-methylaniline (217 μL, 2.0 mmol); NaOtBu (230 mg, 2.4 mmol); Pd(π-crotyl)QPhosCl (7.2 mg, 0.008 mmol, 0.5 mol %); toluene (2.0 mL). The general procedure afforded the title compound in 97% yield (358 mg); $^1$H NMR (CDCl$_3$, 400 MHz): δ 7.30-7.26 (m, 2H), 7.08 (d, J 8.4, 1H), 7.02-6.96 (m, 4H), 6.79 (dd, J 8.4, 2.4, 1H), 3.27 (s, 3H), 2.30 (s, 3H); $^{13}$C (CDCl$_3$, 100 MHz): δ 148.7, 148.1, 134.7, 131.2, 129.4, 128.2, 121.9, 121.0, 120.3, 118.5, 40.4, 19.2; Elemental analysis, found: C 72.01, H 6.04, N 5.98 (theoretical: C 72.57, H 6.09, N 6.04).

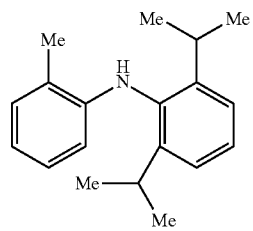

N-(2,6-diisopropylphenyl)-N-(o-tolyl)amine 2-bromotoluene (274 mg, 1.6 mmol) or 2-chlorotoluene (168 μL, 1.6 mmol); 2,6-diisopropylaniline (377 μL, 2.0 mmol); NaOtBu (230 mg, 2.4 mmol); Pd(π-crotyl)QPhosCl (7.2 mg, 0.008 mmol, 0.5 mol %); toluene (2.0 mL). The general procedure afforded the title compound in 96% yield (410 mg; X=Br) and 87% conversion (X=Cl).

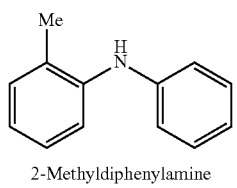 [SMILES: Cc1ccccc1Nc1ccccc1]

2-Methyldiphenylamine 2-bromotoluene (274 mg, 1.6 mmol) or 2-chlorotoluene (168 μL, 1.6 mmol); aniline (182 ∞L, 2.0 mmol); NaOtBu (230 mg, 2.4 mmol); Pd(π-crotyl)QPhosCl (7.2 mg, 0.008 mmol, 0.5 mol %); toluene (2.0 mL). The general procedure afforded the title compound in 91% yield (267 mg; X=Br) and 83% yield (242 mg; X=Cl).

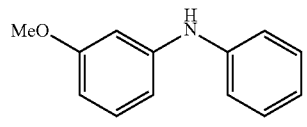

3-Methoxydipheylamine 3-chloroanisole (196 μL, 1.6 mmol); aniline (182 μL, 2.0 mmol); NaOtBu (230 mg, 2.4 mmol); Pd(π-crotyl)QPhosCl (14.4 mg, 0.016 mmol, 1.0 mol %); toluene (2.0 mL). The general procedure afforded the title compound as a white solid in 91% yield (290 mg).

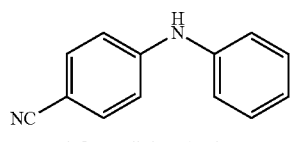

4-Cyanodiphenylamine 4-bromobenzonitrile (292 mg, 1.6 mmol); aniline (182 μL, 2.0 mmol); NaOtBu (230 mg, 2.4 mmol); Pd(π-crotyl)

QPhosCl (14.4 mg, 0.016 mmol, 1.0 mol %); toluene (2.0 mL). The general procedure afforded the title compound as an off-white solid (288 mg, 93%).

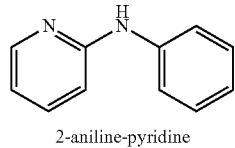 [SMILES: c1ccc(Nc2ccccn2)cc1]

2-aniline-pyridine 2-bromopyridine (153 μL, 1.6 mmol) or 2-chloropyridine (151 μL, 1.6 mmol); aniline (182 μL, 2.0 mmol); NaOtBu (230 mg, 2.4 mmol); Pd(π-crotyl)QPhosCl (28.8 mg, 0.032 mmol, 2.0 mol %); toluene (2.0 mL). The general procedure afforded the title compound in 94% yield (257 mg; X=Br) and 86% yield (235 mg; X=Cl): $^1$H NMR (CDCl$_3$, 400 MHz): δ 8.20 (d, J 4.0, 1H), 7.50-7.46 (m, 1H), 7.33 (d, J 4.0, 4H), 7.08-7.02 (m, 2H), 6.89 (d, J 8.4, 1H), 6.74-6.71 (m, 1H); $^{13}$C (CDCl$_3$, 100 MHz): δ 156.1, 148.4, 140.6, 137.7, 132.5, 129.3, 122.8, 120.7, 120.4, 115.0, 108.2; Elemental analysis, found: C 77.11, H 5.99, N 16.20 (theoretical: C 77.62, H 5.92, N 16.46).

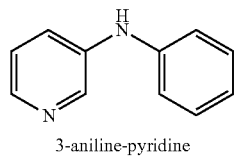 [SMILES: c1ccc(Nc2cccnc2)cc1]

3-aniline-pyridine 3-bromopyridine (154 μL, 1.6 mmol) or 3-chloropyridine (152 μL, 1.6 mmol); aniline (182 μL, 2.0 mmol); NaOtBu (230 mg, 2.4 mmol); Pd(π-crotyl)QPhosCl (28.8 mg, 0.032 mmol, 2.0 mol %); toluene (2.0 mL). The general procedure afforded the title compound in 79% yield (215 mg; X=Br) and 88% yield (239 mg; X=Cl): $^1$H NMR (CDCl$_3$, 400 MHz): δ 8.38 (d, J 2.0, 1H), 8.15 (d, J 4.0, 1H), 7.42 (d, J 7.2, 1H), 7.30 (t, J 7.6, 2H), 7.16 (dd, J 8.0, 4.4, 1H), 7.08 (d, J 8.0, 2H), 6.99 (t, J 7.2, 1H), 6.01 (br s, 1H); $^{13}$C (CDCl$_3$, 100 MHz): δ 142.0, 141.8, 140.1, 139.9, 129.6, 123.8, 123.4, 122.0, 118.3; Elemental analysis, found: C 77.19, H 6.02, N 15.96 (theoretical: C 77.62, H 5.92, N 16.46).

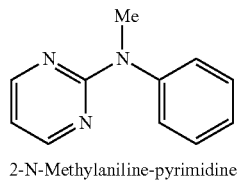 [SMILES: CN(c1ccccc1)c1ncccn1]

2-N-Methylaniline-pyrimidine 2-bromopyrimidine (127 mg, 0.8 mmol); N-methylaniline (109 μL, 1.0 mmol); NaOtBu (115 mg, 1.2 mmol); Pd(π-crotyl)QPhosCl (14.4 mg, 0.016 mmol, 2.0 mol %); toluene (1.0 mL). The general procedure afforded the title compound in 83% yield (123 mg): $^1$H NMR (CDCl$_3$, 400 MHz): δ 8.34 (d, J 4.4, 2H), 7.42 (t, J 8.0, 2H), 7.32 (d, J 7.6, 2H), 7.24-7.22 (m, 1H), 6.57 (t, J 4.8, 1H), 3.53 (s, 3H); $^{13}$C (CDCl$_3$, 100 MHz): δ 162.0, 157.7, 145.5, 129.2, 126.6, 125.9, 110.8, 38.7; Elemental analysis, found: C 71.33, H 6.08, N 22.51 (theoretical: C 71.33, H 5.99, N 22.69).

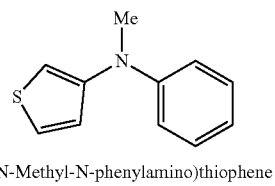

2-(N-Methyl-N-phenylamino)thiophene 3-bromothiophene (150 μL, 1.6 mmol) or 3-chlorothiophene (149 μL, 1.6 mmol); N-methylaniline (217 μL, 2.0 mmol); NaOtBu (230 mg, 2.4 mmol); Pd(π-crotyl)QPhosCl (28.8 mg, 0.032 mmol, 2.0 mol %); toluene (2.0 mL). The general procedure afforded the title compound in 90% yield (272 mg; X=Br) and 57% yield (172 mg; X=Cl): $^1$H NMR (CDCl$_3$, 400 MHz): δ 7.27-7.20 (m, 3H); 7.01 (d, J 7.6, 2H), 6.91 (t, J 7.6, 1 H), 6.87 (dd, J 5.2, 1.6, 1H), 6.57 (dd, J 3.2, 1.2, 1H), 3.29 (s, 3H); $^{13}$C (CDCl$_3$, 100 MHz) δ 149.3, 148.4, 129.1, 124.9, 123.3, 120.7, 118.8, 107.8, 41.0; Elemental analysis, found: C 70.13, H 5.84, N 7.32 (theoretical: C 69.80, H 5.86, N 7.40).

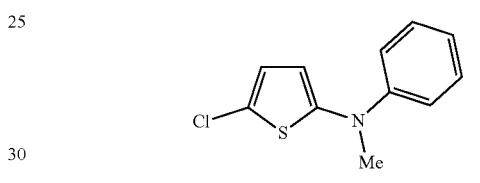

2-Chloro-5-N-methylaniline-thiophene 2-bromo-5-chlorothiophene (175 μL, 1.6 mmol); N-methylaniline (217 μL, 2.0 mmol); NaOtBu (230 mg, 2.4 mmol); Pd(π-crotyl)QPhosCl (28.8 mg, 0.032 mmol, 2.0 mol %); toluene (2.0 mL); 25° C.; 20 hrs. The general procedure afforded the title compound as an off-white oil in 44% yield (155 mg): $^1$H NMR (CDCl$_3$, 400 MHz): δ 7.26-7.23 (m, 2H), 6.94-6.88 (m, 3H), 6.70 (d, J 4.0, 1H), 6.44 (d, J 4.0, 1H), 3.28 (s, 3H); $^{13}$C (CDCl$_3$, 100 MHz): δ 151.3, 148.8, 129.1, 124.6, 123.3, 120.3, 119.1, 116.1, 41.8; Elemental analysis, found: C 59.28, H 4.54, N 6.29 (theoretical: C 59.05, H 4.51, N 6.26).

4-methyldiphenyl-methylamine 4-bromotoluene (274 mg, 1.6 mmol); N-methylaniline (217 μL, 2.0 mmol); NaOtBu (230 mg, 2.4 mmol); Pd(π-crotyl)QPhosCl (0.7 mg, 0.0008, 0.05 mol %); toluene (0.5 mL). The general procedure afforded the title compound in 83% yield (261 mg): $^1$H NMR (CDCl$_3$, 400 MHz): δ 7.24-7.20 (m, 2H), 7.11 (d, J 8.4, 2H), 7.01-6.97 (m, 2H), 6.91 (app. d, J 7.6, 2H), 6.86 (app. t, J 7.6, 1H), 3.28 (s, 3H), 2.31 (s, 3H); $^{13}$C (CDCl$_3$, 100 MHz): δ 149.4, 146.6, 132.1, 130.0, 129.1, 122.6, 119.8, 118.2, 40.4, 20.8; Elemental analysis, found: C 85.25, H 7.75, N 7.29 (theoretical: C 85.24, H 7.66, N 7.10).

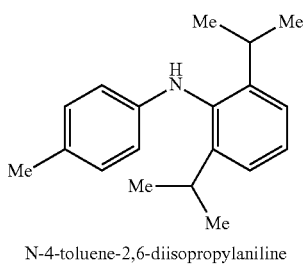 [SMILES: Cc1ccc(Nc2c(C(C)C)cccc2C(C)C)cc1]

N-4-toluene-2,6-diisopropylaniline 4-bromotoluene (274 mg, 1.6 mmol); 2,6-diisopropylaniline (377 μL, 2.0 mmol); NaOtBu (230 mg, 2.4 mmol); Pd(π-crotyl)QPhosCl (0.7 mg, 0.0008, 0.05 mol %); toluene (0.5 mL). The general procedure afforded the title compound in 91% yield (387 mg): $^1$H NMR (CDCl$_3$, 400 MHz): δ 7.30-7.25 (m, 1H), 7.22-7.19 (m, 2H), 6.94 (d, J 8.0, 2H), 6.39 (d, J 8.4, 2H), 5.02 (br s, 1H), 3.19 (heptet, J 6.8, 2H), 2.23 (s, 3H), 1.13 (d, J 6.8, 12H); $^{13}$C (CDCl$_3$, 100 MHz): δ 147.4, 145.9, 135.6, 129.8, 127.0, 126.9, 123.9, 113.1, 28.2, 23.9, 20.5; Elemental analysis, found: C 85.22, H 9.45, N 5.29 (theoretical: C 85.34, H 9.42, N 5.24).

Example 6

N-Arylations at Low Catalyst Loadings of Pd(π-crotyl)QPhosCl

The arylation of amines at lower catalyst loadings were evaluated (Table 7) and, in this respect, reactions carried out with 0.05 or 0.1 mol % loading were successfully achieved.

TABLE 7

N-Arylations at Low Catalyst Loadings of Pd(π-crotyl)QPhosCl.[a]

| Ar—X | amine | X | catalyst loading (mol %) | product | yield (%) |
|---|---|---|---|---|---|
| 4-Me-C$_6$H$_4$-X | PhNHMe | Br<br>Cl | 0.05, 1 h<br>0.10, 1 h | 4-Me-C$_6$H$_4$-N(Me)Ph | 83<br>92 |
| 2-Me-C$_6$H$_4$-X | 2,6-iPr$_2$-C$_6$H$_3$-NH$_2$ | Cl<br>Cl | 0.05, 16 hrs<br>0.1, 2 hrs | 2-Me-C$_6$H$_4$-NH-2,6-iPr$_2$-C$_6$H$_3$ | 90[b]<br>95 |
| 4-Me-C$_6$H$_4$-X | 2,6-iPr$_2$-C$_6$H$_3$-NH$_2$ | Br | 0.05, 2 hrs | 4-Me-C$_6$H$_4$-NH-2,6-iPr$_2$-C$_6$H$_3$ | 91 |

[a]aryl halide (1.6 mmol), amine (2.0 mmol), NaOt-Bu (2.4 mmol), toluene (0.5 mL) [b]GC/MS conversion.

See Example 5 for the experimental data for the products listed in Table 7.

Example 7

Synthesis of the Toddaliopsin Framework

The synthesis of the toddaliopsin framework was realised by implementing a Pd(π-1-crotyl)QPhosCl catalysed aryl amination step incorporating a very electron rich aryl bromide. As can be seen, the C—N coupling reaction proceeded smoothly to provide the required product in 65% yield.

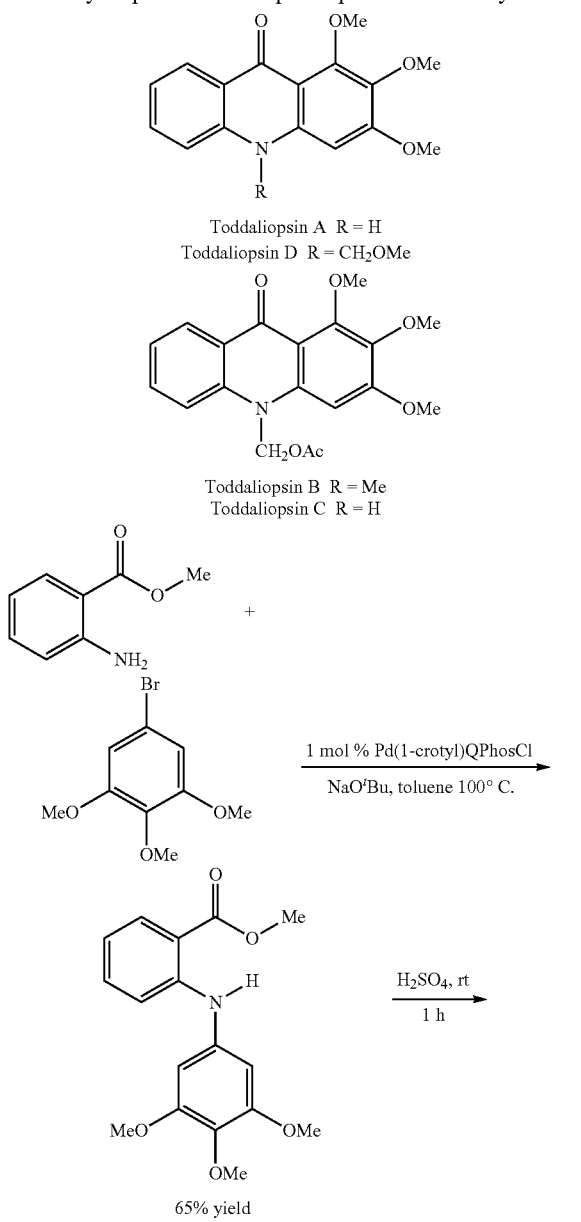

Example 8

General Procedure for the α-Arylation Reaction of Aldehydes

A Schlenk flask was charged with the catalyst, $Cs_2CO_3$ and aryl halide, if solid, and the flask was evacuated and backfilled with nitrogen three times. Subsequently, a solution of the aryl halide, if liquid, and the aldehyde in solvent were added. The resulting reaction mixture was stirred under nitrogen at the indicated temperature for the indicated time, then the mixture was absorbed onto silica gel and purified by flash column chromatography (EtOAc/40-60 petroleum ether eluent).

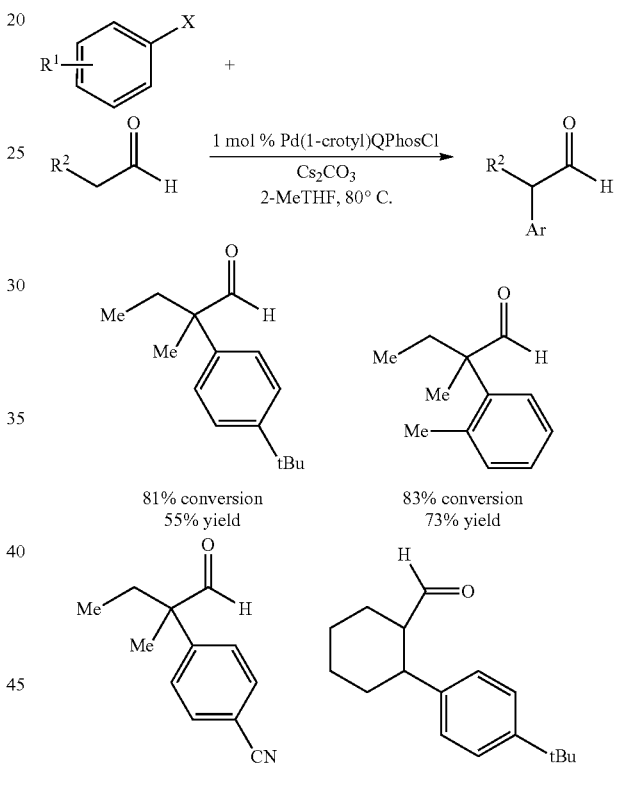

Example 9

General Procedure for the α-arylation of Ketones

A Schlenk flask was charged with the catalyst, NaOtBu and aryl halide, if solid, and the flask was evacuated and backfilled with nitrogen three times. Subsequently, the aryl halide (if liquid), followed by ketone and solvent were added via syringe. The resulting reaction mixture was stirred under nitrogen at the indicated temperature for 18 hours, then the mixture was absorbed onto silica gel and purified by flash column chromatography (MTBE/40-60 petroleum ether eluent).

TABLE 8

α-arylation of ketones

| catalyst (mol %) | solvent | T (° C.) | time (hrs) | Conversion[a] (%) |
|---|---|---|---|---|
| Pd(allyl)QPhosCl (1.0) | THF | 60 | 17 | 76 |
| Pd(1-crotyl)QPhosCl (1.0) | THF | 60 | 17 | 99[b] (85) |
| Pd(1-crotyl)QPhosCl (0.25) | THF | 60 | 17 | (90) |
| Pd(dba)$_2$/QPhos (0.25) (Comparative) | THF | 60 | 17 | (80) |
| Pd(OAc)$_2$/QPhos (0.25) (Comparative) | THF | 60 | 17 | (85) |
| Pd-118 (0.25) (Comparative)[c] | THF | 60 | 17 | (64) |

[a]Conversion using GC/MS. Isolated yield in parenthesis [b]All starting material consumed [c]Pd-118 = dichloro[1,1'-bis(di-tert-butylphosphino)]ferrocene palladium (II)

It can be seen from the results in the above table that the Pd(π-1-crotyl)QPhosCl precatalyst provided the best results in the oc-arylation reaction. Moreover, in comparison with in situ generated QPhos based catalysts, the preformed complexes exhibited comparable or superior activities.

Example 10

Substrate Scope for the α-Arylation of Ketones

It was demonstrated that the mono-arylation of propiophenone proceeded smoothly using a range of electron rich and neutral aryl halides and the Pd(π-1-crotyl)QPhosCl catalyst. Substituents were tolerated in the ortho- and meta- as well as the para-position of the aryl moiety.

TABLE 9

Substrate scope for the α-arylation of ketones

| | 4-MeO-C$_6$H$_4$ | 4-Me-C$_6$H$_4$ | 2-Me-C$_6$H$_4$ |
|---|---|---|---|
| X = Br | 90% yield[b] (0.25 mol %, 60° C.) | 76% yield[a] (0.25 mol %, 60° C.) | 63% yield[a] (0.25 mol %, 60° C.) |
| X = Cl | 82% yield (1.0 mol %, 100° C.) | 61% yield[a] (0.25 mol, 100° C.) | 65% yield[a] (1.0 mol %, 100° C.) |

| | 4-tBu-C$_6$H$_4$ | 3-Me-C$_6$H$_4$ |
|---|---|---|
| X = Br | 88% yield[a] (0.25 mol %, 60° C.) | 99% yield[a] (1.0 mol %, 60° C.) |

[a]Product co-running with propiophenone. Yield given is NMR yield from isolated mixture of product and propiophenone [b]Average yield from 3 reactions

Example 11

α-Arylation of 1-Tetralone

General Procedure

A Schlenk flask was charged with Pd(X)LCl (0.05 mol %, 0.001 mmol) and NaOt-Bu (365 mg, 3.8 mmol). The flask was evacuated and backfilled with nitrogen three times, then dioxane (2.0 ml), 4-chloroanisole (245 μl, 2.0 mmol) and α-tetralone (266 μl, 2.0 mmol) were added. The reaction mixture was stirred for 16 hours, then an aliquot was removed for analysis by GC/MS.

The activities of the π-allyl catalysts bearing the QPhos and P(t-Bu)$_2$(p-NMe$_2$C$_6$H$_4$) ligands were evaluated in the π-arylation of cyclic ketone 1-tetralone. Pd(allyl)QPhosCl provided the product in 80% conversion after 3 hours reaction time, whereas Pd(allyl)P(t-Bu)$_2$(p-NMe$_2$C$_6$H$_4$)Cl gave 96% conversion after the same time (Table 10, entries 1 and 2). The product was isolated in 91% yield after an overnight reaction using catalyst loading as low as 0.05 mol % of Pd(allyl)P(t-Bu)$_2$(p-NMe$_2$C$_6$H$_4$)Cl (entry 3).

TABLE 10

α-Arylation of 1-Tetralone Using 0.05 mol % Pd Loading.[a]

| entry | catalyst | time (hours) | conversion (%)[b] |
|---|---|---|---|
| 1 | Pd(allyl)QPhosCl | 3 | 80 |
| 2 | Pd(allyl)P(t-Bu)$_2$(p-NMe$_2$C$_6$H$_4$)Cl | 3 | 96 |
| 3 | Pd(allyl)P(t-Bu)$_2$(p-NMe$_2$C$_6$H$_4$)Cl | 22 | 100(91) |

[a]4-chloroanisole (2.0 mmol), 1-tetralone (2.0 mmol), NaOt-Bu (3.8 mmol), dioxane (2.0 mL). [b]GC/MS conversion. Average of two runs. Isolated yield in parenthesis.

Example 12

Suzuki Coupling Reactions

General Procedure for the Suzuki Reaction:

A Schlenk flask was charged with the catalyst, KOtBu (1.2 eq), boronic acid (1.1 eq) and aryl halide (1.0 eq), if solid, and the flask was evacuated and backfilled with nitrogen three times. Subsequently, the aryl halide (if liquid) and solvent were added via syringe. The resulting reaction mixture was stirred under nitrogen at the indicated temperature, then the crude reaction mixture was analysed by GC/MS.

TABLE 11

Suzuki coupling reactions

| X | solvent | C (M) | loading (mol %) | time (h) | T (° C.) | conversion (%)[a] |
|---|---|---|---|---|---|---|
| Br | toluene:H$_2$O (4:1) | 0.8 | 0.01 | 20 | 100 | 100 |
| Br | toluene:H$_2$O (4:1) | 0.8 | 1.0 | 1 | 25 | 100 |
| Cl | toluene | 0.27 | 1.0 | 20 | 80 | 68 |

[a]conversion into product, taking into account deboronated product formed.

The high activity of Pd(crotyl)Q-PhosCl was subsequently demonstrated in the sterically challenging Suzuki reaction of bromomesitylene and 1-naphthalene boronic acid. This coupling could be carried out at ambient temperature with 100% GC conversion and 86% isolated yield within 45 minutes of the reaction time.

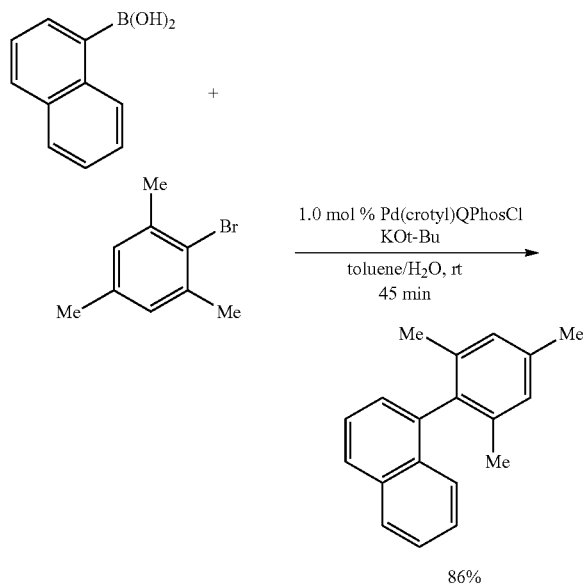

Example 13

Aryl Chlorides in Suzuki Coupling

Extending the scope of the substrates to aryl chlorides, the coupling product of of 4-chloroanisole with 4-tert-butylbenzene boronic acid gave 90% conversion (Table 12, entry 1) using the same reaction conditions as for the aryl bromides, but at 80° C. The present inventors also decided to investigate the base effect and the use of heterocyclic chlorides employing the π-allyl catalysts in comparision with the use of $PdCl_2(P(t-Bu)_2(p-NMe_2C_6H_4))_2$ as reported by Guram (Guram et al, Org. Lett., 2006, 8, 1787). Substituting $K_2CO_3$ for KOt-Bu in the case of 4-chloroanisole provided the coupling product in relatively low conversions, using both Pd(crotyl)QPhosCl and $Pd(allyl)P(t-Bu)_2(p-NMe_2C_6H_4)Cl$ (entries 2 and 3). However, employing 2-chlorothiophene in the Suzuki reaction, it was found that the yield of the product was comparable to the Guram conditions for $PdCl_2(P(t-Bu)_2(p-NMe_2C_6H_4))_2$ and the new Pd(allyl) $P(t-Bu)_2(p-NMe_2C_6H_4)Cl$ (entries 4-5, 6-7, 8-9), demonstrating that a Pd:L ratio of 1:1 was sufficient for an efficient reaction. Using the reaction conditions developed for the aryl bromides, 2-chlorothiophene was coupled with 4-tert-butylbenzene boronic acid to obtain 52% yield, with Pd(crotyl) QPhosCl catalyst (entry 10). The same reaction gave a lower yield (33%) under the Guram conditions (entry 11). For chloropyridine substrate, Pd(π-allyl)AmphosCl gave 73% yield (entry 13).

The described investigation of aryl chlorides in Suzuki coupling illustrates the importance of a careful choice of the catalyst and the reaction conditions to get the optimized yields.

TABLE 12

Aryl Chlorides in Suzuki Coupling.[a]

| Entry | catalyst | conditions | RB(OH)₂ | Ar—Cl | | yield (%)[a] |
|---|---|---|---|---|---|---|
| 1 | 1 mol % Pd(1-crotyl)QPhosCl | A | 4-tBu-C₆H₄-B(OH)₂ | 4-MeO-C₆H₄-Cl | 4-tBu-C₆H₄-C₆H₄-OMe | 90[b] |
| 2 | 1 mol % Pd(1-crotyl)QPhosCl | B | 4-tBu-C₆H₄-B(OH)₂ | 4-MeO-C₆H₄-Cl | 4-tBu-C₆H₄-C₆H₄-OMe | 38[b] |
| 3 | 1 mol % Pd(allyl)AmphosCl | B | 4-tBu-C₆H₄-B(OH)₂ | 4-MeO-C₆H₄-Cl | 4-tBu-C₆H₄-C₆H₄-OMe | 29[b] |

TABLE 12-continued
Aryl Chlorides in Suzuki Coupling.[a]
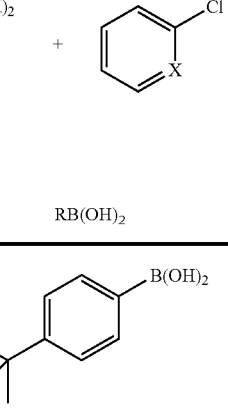
| Entry | catalyst | conditions | RB(OH)$_2$ | Ar—Cl | yield (%)$_a$ |
|---|---|---|---|---|---|
| 4 | 1 mol % Pd(allyl)AmphosCl | B | 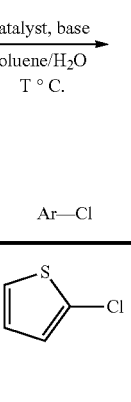 | 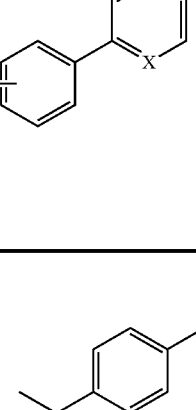 | 64 |
| 5[c] | 1 mol % Pd-132 | | | | 68 |
| 6 | 1 mol % Pd(allyl)AmphosCl | B | 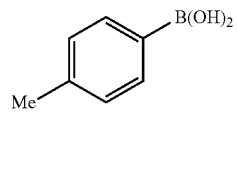 | 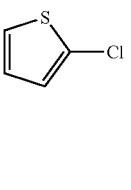 | 70 |
| 7[c] | 1 mol % Pd-132 | | | | 84 |
| 8 | 0.01 mol % Pd(allyl)AmphosCl | B | 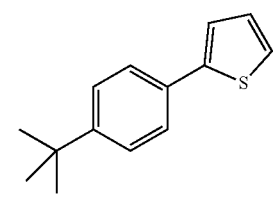 | 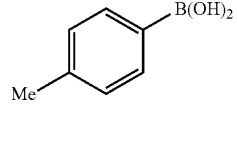 | 85 |
| 9[c] | 0.01 mol % Pd-132 | | | | 79 |
| 10 | 1 mol % Pd(1-crotyl)QPhosCl | A | 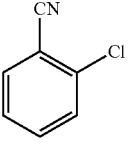 | 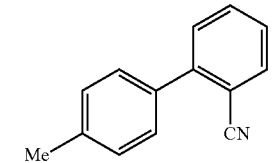 [SMILES: Cc1ccc(-c2ccccc2C#N)cc1] | 52 |
| 11 | 1 mol % Pd(1-crotyl)QPhosCl | B | 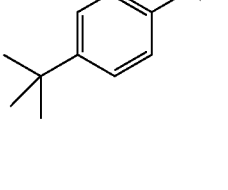 | 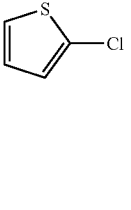 | 33 |
| 12 | 1 mol % Pd(1-crotyl)AmphosCl | B | 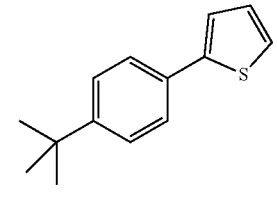 | 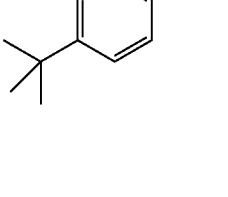 | 29 |
Products (entries 4–12):
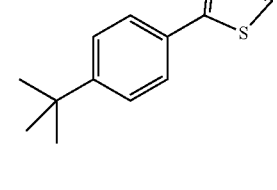
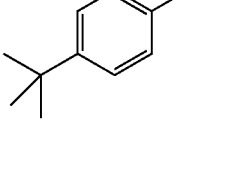
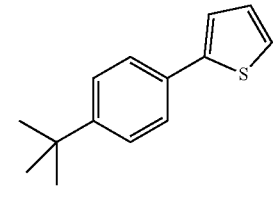

TABLE 12-continued

Aryl Chlorides in Suzuki Coupling.[a]

| Entry | catalyst | conditions | RB(OH)$_2$ | Ar—Cl | yield (%)$_a$ |
|---|---|---|---|---|---|
| 13 | 1 mol % Pd(allyl)AmphosCl | B | 4-tert-butylphenyl-B(OH)$_2$ | 3-chloropyridine | 73 |

[a]Conditions A: aryl chloride (1.6 mmol), boronic acid (1.76 mmol), KOt-Bu (1.92 mmol), toluene (1.8 mL), water (0.2 mL), 80° C. Conditions B: aryl chloride (1.0 mmol), boronic acid (1.2 mmol), K$_2$CO$_3$ (2.0 mmol), toluene (5.0 mL), water (0.5 mL), 100° C. Isolated yield. [b]GC/MS conversion. [c]Pd-132 ; PdCl$_2$[P(t-Bu)$_2$(p-NMe$_2$C$_6$H$_4$]$_2$.

In the Suzuki coupling reactions, the present inventors have been the first to demonstrate that K$_2$CO$_3$ can be used as the base in conjunction with π-allyl precatalysts.

What is claimed is:

1. A complex of formula (1):

$$\text{(1)}$$

wherein:
M is palladium or nickel,
R$_1$ and R$_2$ are, independently, C$_{1-20}$ straight-chain alkyl, C$_{1-20}$ branched-chain alkyl, or C$_{3-15}$ cycloalkyl,
R$_3$ is a) or b):
  a) substituted aryl, wherein the aryl is substituted with one or more halide, C$_{2-20}$ alkoxy, substituted C$_{6-20}$ aryl, branched-chain (C$_{1-20}$ dialkyl)amino, C$_{2-15}$ heterocycloalkyl, or tri(halo)methyl; or
  b) substituted or unsubstituted heteroaryl that is thienyl, furanyl, pyrrolyl, imidazolyl, pyrazolyl, thiazolyl, isothiazolyl, oxazolyl, isoxazolyl, triazolyl, thiadiazolyl, thiophenyl, oxadiazolyl, pyridinyl, pyrimidyl, benzoxazolyl, benzthiazolyl, benzimidazolyl, indolyl, or quinolinyl;
R$_4$ is C$_{1-20}$ straight-chain alkyl, C$_{1-20}$ branched-chain alkyl, C$_{3-15}$ cycloalkyl, C$_{6-20}$ aryl, or C$_{5-20}$ heteroaryl;
n is 0, 1, 2, 3, 4 or 5,
X is halo;
wherein each alkyl, alkoxy, heteroalkyl, aryl or heteroaryl is optionally substituted with one or more halo, C(halo)$_3$, R$^a$, =O, =S, OR$^a$, SR$^a$, NR$^a$R$^b$, =NR$^a$, =N—OR$^a$, CN, SCN, NCS, NO$_2$, C(O)R$^a$, C(O)OR$^a$, C(S)R$^a$, C(S)OR$^a$, S(O)$_2$OH, S(O)$_2$R$^a$, S(O)$_2$NR$^a$R$^b$, OS(O)R$^a$, or C(O)NR$^a$R$^b$, wherein:
  R$^a$ and R$^b$ are, independently, H, C$_{1-20}$ alkyl, C$_{6-20}$ aryl, C$_{6-20}$ aryl-(C$_{1-20}$alkyl), C$_{1-20}$ heteroalkyl, or C$_{6-20}$ heteroaryl, or together with the atom to which they are attached form a C$_{3-15}$ heterocycloalkyl; and the heteroatoms in the heteroaryl, heteroalkyl or heterocycloalkyl are sulfur, oxygen, or nitrogen.

2. The complex of claim 1, wherein M is palladium.

3. The complex of claim 1, wherein R$_1$ and R$_2$ are tert-butyl.

4. The complex of claim 1, wherein R$_1$ and R$_2$ are cyclohexyl.

5. The complex of claim 1, wherein R$_3$ is furanyl, thiophenyl, pyrrolyl, pyridinyl, or quinolinyl.

6. The complex of claim 1, wherein X is Cl.

7. The complex of claim 1, wherein each R$_4$ is independently methyl, phenyl, or substituted phenyl.

8. A method for preparing a complex of formula (1):

$$\text{(1)}$$

comprising the step of reacting a complex of formula (5) with PR$_1$R$_2$R$_3$, $$\text{(5)}$$

wherein:
M is palladium or nickel,
R$_1$ and R$_2$ are, independently, C$_{1-20}$ straight-chain alkyl, C$_{1-20}$ branched-chain alkyl, or C$_{3-15}$ cycloalkyl;
R$_3$ is a) or b):
  a) substituted aryl, wherein the aryl is substituted with one or more halide, C$_{2-20}$ alkoxy, substituted C$_{6-20}$ aryl, branched-chain (C$_{1-20}$ dialkyl)amino, C$_{2-15}$ heterocycloalkyl, or tri(halo)methyl; or
  b) substituted or unsubstituted heteroaryl that is thienyl, furanyl, pyrrolyl, imidazolyl, pyrazolyl, thiazolyl, isothiazolyl, oxazolyl, isoxazolyl, triazolyl, thiadiazolyl, thiophenyl, oxadiazolyl, pyridinyl, pyrimidyl, benzoxazolyl, benzthiazolyl, benzimidazolyl, indolyl, or quinolinyl;

$R_4$ is $C_{1-20}$ straight-chain alkyl, $C_{1-20}$ branched-chain alkyl, $C_{3-15}$ cycloalkyl, $C_{6-20}$ aryl, or $C_{5-20}$ heteroaryl;

n is 0, 1, 2, 3, 4 or 5;

X is halo;

wherein each alkyl, alkoxy, heteroalkyl, aryl or heteroaryl is optionally substituted with one or more halo, $C(halo)_3$, $R^a$, =O, =S, $OR^a$, $SR^a$, $NR^aR^b$, =$NR^a$, =N—$OR^a$, CN, SCN, NCS, $NO_2$, $C(O)R^a$, $C(O)OR^a$, $C(S)R^a$, $C(S)OR^a$, $S(O)_2OH$, $S(O)_2R^a$, $S(O)_2NR^aR^b$, $OS(O)R^a$, or $C(O)NR^aR^b$, wherein:

$R^a$ and $R^b$ are, independently, H, $C_{1-20}$ alkyl, $C_{6-20}$ aryl, $C_{6-20}$ aryl-($C_{1-20}$alkyl), $C_{1-20}$ heteroalkyl, or $C_{6-20}$ heteroaryl, or together with the atom to which they are attached form a $C_{3-15}$ heterocycloalkyl; and the heteroatoms in the heteroaryl, heteroalkyl or heterocycloalkyl are sulfur, oxygen, or nitrogen.

9. A method for performing a carbon-carbon coupling reaction or a carbon-nitrogen coupling reaction in the presence of a catalyst, the method comprising using a catalyst that is a complex of claim 1.

10. A method for performing a carbon-carbon coupling reaction or a carbon-nitrogen coupling reaction in the presence of a catalyst, the method comprising using a catalyst that is a complex of claim 2.

* * * * *